US012595467B2

(12) United States Patent
Larsen et al.

(10) Patent No.: US 12,595,467 B2
(45) Date of Patent: Apr. 7, 2026

(54) DNA POLYMERASE AND DNA POLYMERASE DERIVED 3'-5'EXONUCLEASE

(71) Applicant: Universitetet I Tromsø—Norges Arktiske Universitet, Langnes (NO)

(72) Inventors: Atle Noralf Larsen, Kvaløya (NO); Yvonne Piotrowski, Tromsø (NO)

(73) Assignee: Universitetet I Tromsø—Norges Arktiske Universitet, Tromsø (NO)

( * ) Notice: Subject to any disclaimer, the term of this patent is extended or adjusted under 35 U.S.C. 154(b) by 643 days.

(21) Appl. No.: 17/765,645

(22) PCT Filed: Oct. 1, 2020

(86) PCT No.: PCT/EP2020/077531
§ 371 (c)(1),
(2) Date: Mar. 31, 2022

(87) PCT Pub. No.: WO2021/064106
PCT Pub. Date: Apr. 8, 2021

(65) Prior Publication Data
US 2023/0332118 A1 Oct. 19, 2023

(30) Foreign Application Priority Data

Oct. 1, 2019 (EP) ..................................... 19200786

(51) Int. Cl.
| | |
|---|---|
| *C12N 9/16* | (2006.01) |
| *C12N 9/12* | (2006.01) |
| *C12N 15/63* | (2006.01) |
| *C12P 19/34* | (2006.01) |

(52) U.S. Cl.
CPC ............. *C12N 9/16* (2013.01); *C12N 9/1252* (2013.01); *C12N 15/63* (2013.01); *C12P 19/34* (2013.01); *C12Y 301/11* (2013.01)

(58) Field of Classification Search
None
See application file for complete search history.

(56) References Cited

U.S. PATENT DOCUMENTS

| | | | |
|---|---|---|---|
| 10,316,359 B2 | 6/2019 | Makarov et al. | |
| 2019/0119706 A1* | 4/2019 | Tappel | .................... C12P 7/625 |

FOREIGN PATENT DOCUMENTS

| | | |
|---|---|---|
| EP | 1915446 B1 | 4/2008 |
| EP | 1929012 B1 | 6/2008 |
| WO | 2007124065 A1 | 11/2007 |
| WO | 2009103027 A2 | 8/2009 |
| WO | 2010094693 | 8/2010 |
| WO | 2016026574 A1 | 2/2016 |
| WO | 2017162765 A1 | 9/2017 |

OTHER PUBLICATIONS

Byrnes et al., A New Mammalian DNA Polymerase with 3' to 5' Exonuclease Activity, Biochemistry 15, 1976, 2817. (Year: 1976).*
Petrov et al., Protein Determinants of RNA Binding by DNA Polymerase of the T4-related Bacteriophage RB69, J. Biol. Chem. 277, 2002, 33041-48. (Year: 2002).*
Genbank, Accession No. Q38087, 2017, www.uniprot.org. (Year: 2017).*
Uniprot, Accession No. A0A090IAP3, 2019, www.uniprot.org. (Year: 2019).*
Database geneseq [Online] Nov. 26, 2014 (Nov. 26, 2014), "DNA polymerase"; retrieved from EBI Accession No. Uniprot:A0A090IAP3.
Database geneseq [Online] Sep. 30, 2014 (Sep. 30, 2014), "Moritella viscosa genome assembly, chromosome: 1"; retrieved from EBI Accession No. EM_STD:LN554852.
European Search Report for European Application 19200786.2 [PCT/EP2020/077531] dated Feb. 14, 2020; 7 pages.
Fijalkowska, I. et al.; "DNA replication fidelity in *Escherichia coli*: a multi-DNA polymerase affair"; FEMS Microbiology Review, vol. 36, Issue No. 6; 2012; pp. 1105-1121.
International Search Report and Written Opinion for Interantional Application PCT/EP2020/077531; International Filing Date: Oct. 1, 2020; Date of Mailing: Jan. 12, 2021; 11 pages.
Li, et al.; "SLIC: a method for sequence and ligation independent cloning"; Gene Synthesis, vol. 852; 2012; pp. 51-59.
Lunder, et al.; "Winter ulcer' in the Atlantic salmon Salmo salar. Pathological and bacteriological investigations and transmission experiments"; Disease of Aquatic Organisms, vol. 23, Issue No. 23; 1995; pp. 39-49.
McWilliam, et al.; "Analysis Tool Web Services from the EMBL-EBI"; Nucleic Acids Research, vol. 41; 2013; pp. W597-W600.
Sievers, F. et al.; "Clustal Omega for making accurate alignments of many protein sequences"; Protein Science, vol. 27; 2018; pp. 135-145.
Summerer, D.; "DNA Polymerase Profiling"; Methods of Molecular Biology, vol. 429; 2008; pp. 225-235; DOI: 10.1007/978-1-60327-040-3_16.
Blasco, M. et al.; "ø29 DNA Polymerase Active Site: Residue ASP249 of Conserved Amino Acid Motif "DX2SLYP" Is Critical for Synthetic Activities"; The Journal of Biological Chemistry, vol. 268, Issue No. 32; 1993; pp. 24106-24113.

(Continued)

*Primary Examiner* — Todd M Epstein
(74) *Attorney, Agent, or Firm* — Karen LeCuyer; DeWitt LLP

(57) ABSTRACT

The present invention relates to enzymes having DNA polymerase and 3'-5' exonuclease activities. In particular, the present invention relates to a heat labile enzyme possessing a DNA polymerase II activity and a 3'-5' exonuclease activity of marine origin. Furthermore, the present invention relates to a DNA polymerase primarily exerting a 3'-5' activity, i.e. where the polymerase activity is absent. The present invention furthermore relates to the use of the exonuclease activity to degrade the 3'-5' strand of double stranded DNA to perform single stranded overhang, e.g. in recombinant cloning processes, or in processes for removal of contaminating nucleic acid molecules.

12 Claims, 5 Drawing Sheets
Specification includes a Sequence Listing.

(56)            References Cited

OTHER PUBLICATIONS

First Office Action for CN Application No. 2020800693600 dated Jul. 10, 2024, with English translation.
Notification of Reasons for Rejection for JP Application No. 2022-520324 dated Jul. 16, 2024, with English translation.
Moritella viscosa genome assembly MVIS1 , chromosome : 1—Sequence ID: LN554852.1, NCBI Blast: Nucleiotide Sequence. 2024.
DNA polymerase II [Moritella viscosa], NCBI Reference Sequence: WP_045109450.1, NCBI, 2019/07/27, p. 1, https://www.ncbi.nlm.nih.gov/protein/769993843?sat=49&satkey=24722418 [Date of search: Jul. 4, 2024].
DNA polymerase II [*Moritella* sp. JT01], NCBI Reference Sequence: WP_067047775.1, NCBI, 2016, p. 1, https://www.ncbi.nlm.nih.gov/protein/1055384593?sat=47&satkey=113878131 [Date of search: Jul. 4, 2024].
Blanco, Luis & Salas, Margarita. Mutational Analysis of Bacteriophage Ø29 DNA Polymerage Methods in Enzymology, 1995, vol. 262, pp. 283-294.

* cited by examiner

FIG. 2

DNA POLYMERASE AND DNA POLYMERASE DERIVED 3'-5'EXONUCLEASE

CROSS REFERENCE TO RELATED APPLICATIONS

This application is a National Stage application of PCT/EP2020/077531, filed Oct. 1, 2020, which claims priority to European Patent Application No. 19200786.2, filed Oct. 1, 2019, both of which are incorporated by reference in their entirety herein.

SEQUENCE LISTING

The Instant Application contains a Sequence Listing which has been submitted electronically in ASCII format and is hereby incorporated by reference in its entirety. Said ASCII copy, created on Aug. 18, 2022 is named "OSA0070US Replacement Sequence List ST25" and is 61,906 bytes in size.

FILED OF INVENTION

The present invention relates to enzymes having DNA polymerase and 3'-5' exonuclease activities. In particular, the present invention relates to a heat labile enzyme possessing a DNA polymerase II activity and a 3'-5' exonuclease activity of marine origin. Furthermore, the present invention relates to a DNA polymerase primarily exerting a 3'-5' activity, i.e. where the polymerase activity is absent. The present invention furthermore relates to the use of the exonuclease activity to degrade the 3'-5' strand of double stranded DNA to perform single stranded overhang, e.g. in recombinant cloning processes, or in processes for removal of contamination nucleic acid molecules.

BACKGROUND OF INVENTION

Synthetic biology is a rapidly evolving field and is heralded as a possible solution for the challenges in future bio-economy and bioenergy. The ultimate vision of synthetic biology is to create new biological operating systems of cells that predictably can carry out useful tasks. One of the key steps in a synthetic biology pipeline is the assembly of DNA fragments into larger functional constructs often involving multiple assemblies.

A current bottleneck is however the lack of a robust room-temperature method to do multiple DNA assemblies without time-consuming manual treatment steps. A new DNA assembly method able to bypass the current hurdles is therefore highly desired.

Replication of genomic DNA is the primary function of DNA polymerases, catalysing the synthesis for polydeoxyribonucleotides from mono-deoxyribonucleoside triphosphate (dNTPs).

In vitro, the characteristics of DNA polymerases are used in DNA synthesis, such as in various DNA amplification processes and in synthesis of DNA molecules reading a DNA strand template of interest creating two new DNA strands that match the template.

Different types of polymerases are found. For example, in *E. coli* and other prokaryotic cells, the known DNA polymerases are commonly referred to as DNA polymerase I-V. The various groups vary in fidelity of replication, thermostability, elongation rate, and proof-reading activity and efficiency. Some DNA polymerases are rather simple and others more complex, such as *E. coli* polymerase III that consist of 20 different peptide subunits.

Many of the widely used DNA polymerases are stable at high temperatures, such as up to at least 70° C. thus enabling their use in DNA detection and analysis methods, such as polymerase chain reaction (PCR) or thermocycled DNA sequencing. DNA polymerases applicable in such processes are commonly named thermostable DNA polymerases.

When used in DNA replication processes in vitro, in addition to dNTPs, a primer (an initial oligonucleotide) is needed, carrying a 3'end hydroxyl group that can be used as the starting point of chain growth, since DNA polymerases cannot initiate synthesis de novo from mononucleotides. The primer can be a short or long piece of DNA or RNA which carries a free 3'-OH group, providing a double-stranded structure to the DNA polymerase by annealing to a complementary region of a template. The selected DNA polymerase works along the template, extending the primer in the 5'→3' direction.

Because of DNA strand polarity, replication of the two strands of a DNA molecule are bidirectional resulting in in two distinct products, a "leading" and a "lagging" strands, according to the direction of the replication of the template. The leading strand is synthesized as a single continuous chain, whereas the lagging strand is initially synthesized as small oligonucleotides, called Okazaki fragments, which are then ligated to form a continuous chain. In vivo, small RNA molecules work as natural primers in the synthesis of both the leading strand and, in particular, the lagging strand.

It is well known that DNA polymerase III synthesize continuously the leading strand and also the Okazaki fragments on the lagging strand, leaving gaps between the synthesized fragments that are thereafter filled by DNA polymerase I.

In addition to the DNA synthesis activity, DNA polymerases may also exert other enzyme activities, such as 3'-5' exonuclease activities or strand displacement activities. In vivo, the 3'-5' exonuclease activity of some of the DNA polymerases is important for genetic stability, correcting DNA polymerase errors, that e.g. results in mismatched base pair in the resulting DNA molecule that is then corrected by the exonuclease function of DNA polymerases. DNA polymerase II is known to have an efficient 3'-5 exonuclease activity, e.g. correcting mismatch errors produced by DNA polymerase III, and are also believed to be involved in repair of post synthesis damage of DNA, such as e.g. due to UV irradiation.

In order to substitute and correct a mismatched base pair, the proof-reading activity of DNA polymerases must be able to remove the incorrectly introduced dNTP and the nuclease activity therefore involved the breaking of the phosphodiester bond in the phosphate backbone of DNA molecules. The ability to remove a mismatched dNTP and thus degrade DNA is utilized in various ways in in vitro molecular biology.

Various enzymes of marine origin are known. For example, WO2017/162765 discloses a thermostable DNA polymerase of marine origin isolated from *Psychrobacillus* sp. being active at a wide range of temperatures, including temperatures above room temperature.

WO2016026574 discloses a thermolabile exonuclease originating from a cold-water environment being capable of degrading single stranded DNA, and which may be inactivated within 15-20 minutes if exposed to temperatures below 65° C.

The present inventors have identified a heat labile DNA polymerase II originating from *Moritella viscosa* surprisingly found to have a very strong 3'-5' exonuclease activity in absence of dNTPs. The enzyme of the present invention was identified in a *M. viscosa* strain from farmed Atlantic salmon affected by winter ulcer disease as disclosed further below in the experimental part.

In particular, it was found that the present exonuclease is able to bind double stranded DNA molecules and degrade the ends thereof in 3'-5' direction, resulting in 5'overhang in both ends of DNA molecules subjected to the DNA polymerase derived 3'-5 exonucleases of the present invention.

Furthermore, the identified enzyme of the present invention was also found to have very poor polymerase activity at room temperature.

A further advantage of the identified DNA polymerase derived 3'-5' exonuclease is that the temperature for optimal activity is around room temperature. Furthermore, the enzyme of the present invention has been shown to be easily inactivated at temperatures above 25° C., such as above about 30° C., resulting in that the exonuclease activity will cease after a while if used at temperature about 25° C. Thus, when e.g. used to prepare 5' overhang, overhang of suitable lengths may be formed e.g. within about 5-30 minutes.

The combination of 3'-5 exonuclease activity, poor polymerase activity and heat lability render the enzyme useful in molecular cloning, polynucleotide removal and DNA assembly processes as further shown below.

Yet an advantage of the present DNA polymerase derived 3'-5' exonuclease, is that the exonuclease activity is active also in presence of dNTPs. Thus, the present enzyme can be used e.g. to prepare 5' overhang without pre-purification processes aiming at removing dNTPs.

In order to be able to make use of the exonuclease activity only, the present inventors have also synthesized modified variants of the DNA polymerase of the present invention, wherein the polymerase activity is sufficiently impaired or absent.

SUMMARY OF INVENTION

According to a first aspect, an isolated DNA polymerase derived 3'-5'exonuclease or an enzymatically active fragment thereof is provided, wherein said DNA exonuclease is substantially without polymerase activity and wherein said enzyme is irreversibly inactivated at temperatures above 25° C., such as at temperatures above about 30° C.

According to a second aspect, an isolated DNA polymerase derived 3'-5'exonuclease or an enzymatically active fragment thereof is provided, wherein said DNA polymerase comprising the amino acid sequence of SEQ ID No. 1 or comprising an amino acid sequence which is at least 60% sequence identical over the entire length of the sequence with SEQ ID No. 1.

According to a third aspect, an isolated DNA polymerase derived 3'-5'exonuclease or an enzymatically active fragment thereof is provided, said DNA polymerase comprising the amino acid sequence of SEQ ID No. 2, or comprising an amino acid sequence which is at least 60% sequence identical over the entire length of the sequence with SEQ ID No. 2.

The isolated DNA polymerase derived 3'-5'exonuclease or an enzymatically active fragment thereof according to the second and third aspect may comprise an amino acid sequence which is at least 70% identical over the entire length of the sequence with SEQ ID No. 1 or SEQ ID No. 2, such as at least 80% sequence identical over the entire length of the sequence with SEQ ID No. 1 or SEQ ID No. 2, such as at least 90% sequence identical over the entire length of the sequence with SEQ ID No. 1 or SEQ ID No. 2.

According to a forth aspect, an isolated DNA polymerase or an enzymatically active fragment thereof is provided, wherein said polymerase comprises and amino acid sequences comprising at least one mutation in at least one of the amino acid regions corresponding to an amino acid positions V440-Y447 and positions G519-A523.

According to one embodiment of the above aspect, said DNA polymerase comprises at least one mutation in amino acid positions corresponding to D442, S445 and/or D568, wherein the at least one mutation is a substitution to:

an amino acid with a hydrophobic side chain in the position corresponding to D442;

an amino acid with a hydrophobic side chain in the position corresponding to S445; and/or an amino acid with a hydrophobic side chain in the position corresponding to D568.

For example, said DNA polymerase derived 3'-5'exonuclease may according one embodiment of the above aspect comprise an amino acid sequence, wherein at least one mutation in amino acid positions corresponding to D442 and/or D568 of an amino acid sequence as set forth in SEQ ID No. 1 and SEQ ID No. 2.

Furthermore, said DNA polymerase derived 3'-5'exonuclease may according another embodiment of the above aspect comprise an amino acid sequence, wherein at least one mutation in amino acid positions corresponding to D442 and/or D568 of an amino acid sequence as set forth in SEQ ID No. 1 and SEQ ID No. 2, and wherein the at least one mutation is a substitution to an amino acid with a hydrophobic side chain at position corresponding to D442, S445 and/or D568.

Furthermore, said DNA polymerase derived 3'-5'exonuclease may according another embodiment of the above aspect comprise an amino acid sequence, wherein the amino acid in position 442 according to the numbering of SEQ ID No. 1 or SEQ ID No. 2 is selected from the group consisting of Glu, Asp, Ala, Gly, Val, Leu, and Ile.

Furthermore, said DNA polymerase derived 3'-5'exonuclease may according another embodiment of the above aspect comprise an amino acid sequence, wherein the amino acid in position 658 according to the numbering of SEQ ID No. 1 or SEQ ID No. 2 is selected from the group consisting of Glu, Asp, Ala, Gly, Val, Leu, and Ile.

Furthermore, said DNA polymerase derived 3'-5'exonuclease may according another embodiment of the above aspect comprise an amino acid sequence, wherein the amino acid in position 445 according to the numbering of SEQ ID No. 1 or SEQ ID No. 2 is selected from the group consisting of Ser, Arg, Lys, and His.

Furthermore, said DNA polymerase derived 3'-5'exonuclease may according another embodiment of the above aspect comprise an amino acid sequence, wherein the amino acid in position 442, 445 and 568 is selected from the groups consisting of

| Amino acid position of SEQ ID No. 1 | Amino acid |
| --- | --- |
| 442 | Asp, Glu, Ala, Gly, Val, Leu, Ile |
| 445 | Ser, Arg, Lys, His |
| 568 | Asp, Glu, Ala, Gly, Val, Leu, Ile | provided that the amino acids in position 442 (D442), 445 (S445) and 568 (D568) are not at the same time Asp, Ser and Asp, respectively.

Furthermore, said DNA polymerase derived 3'-5'exonuclease may according another embodiment of the above aspect comprise an amino acid sequence, wherein the amino acid in position 442 and 568 is selected from the groups consisting of

| Amino acid position of SEQ ID No. 1 | Amino acid |
| --- | --- |
| 442 | Asp, Glu, Ala |
| 445 | Ser, Arg |
| 568 | Asp, Glu, Ala | provided that the amino acids in position 442 (D442), 445 (S445) and 568 (D568) are not at the same time Asp, Ser and Asp, respectively.

In one embodiment according to any of the above aspects the isolated DNA polymerase derived 3'-5'exonuclease or an enzymatically active fragment thereof is a DNA polymerase derived 3'-5'exonuclease selected from a group of DNA polymerases derived 3'-5'exonucleases comprising an amino acid sequence wherein the amino acid in position 442 is Ala;
the amino acid in position 568 is Ala;
the amino acid in position 442 is Glu;
the amino acid in position 568 is Glu;
the amino acid in position 442 and 568 is Ala; and
the amino acid in position 445 is Arg and wherein the numbering is according to amino acid sequence of SEQ ID No. 1.

The DNA polymerase derived 3'-5'exonuclease according to the above embodiment is a DNA polymerase II derived 3'-5'exonuclease substantially without polymerase activity and wherein said enzyme is irreversibly inactivated at temperatures above 25° C., such as at temperatures above about 30° C.

According to a sixth aspect, an isolated DNA polymerase derived 3'-5'exonuclease or an enzymatically active fragment thereof is provided, said DNA polymerase derived 3'-5'exonuclease comprising an amino acid sequence selected from the group consisting of SEQ ID No. 3, 4, 5, 6, 7 and 8, or comprising an amino acid sequence which is at least 60%, such as at least 70%, such as at least 75%, such as at least 80%, such as at least 85% such as at least 90%, such as at least 95%, such as at least 97%, such as at least 98% or 99% sequence identical over the entire length of the sequence with SEQ ID No. 3, 4, 5, 6, 7, and 8, respectively, provided that the amino acid in position 442 in SEQ ID No. 3 is Ala;
the amino acid in position 568 in SEQ ID No. 4 is Ala;
the amino acid in position 442 in SEQ ID No. 5 is Glu;
the amino acid in position 568 in SEQ ID No. 6 is Glu;
the amino acid in position 442 and 568 in SEQ ID No. 7 is Ala; and
the amino acid in position 445 in SEQ ID No. 8 is Arg.

According to another embodiment of any of the above aspects, the isolated DNA polymerase derived 3'-5'exonuclease is a DNA polymerase II derived 3'-5'exonuclease.

According to another embodiment, an isolated DNA polymerase derived 3'-5'exonuclease or an enzymatically active fragment thereof according to the present invention is provided, wherein the enzyme is irreversibly inactivated at temperatures above 25° C., such as at temperatures above 30° C.

According to a seventh aspect, a composition is provided comprising an isolated DNA polymerase derived 3'-5'exonuclease or an enzymatically active fragment thereof according to any of the preceding claims and a buffer.

According to an eight aspect, a nucleic acid molecule is provided, encoding an isolated DNA polymerase derived 3'-5'exonuclease according to the present invention or an enzymatically active fragment thereof.

According to one embodiment of the eight aspect, a nucleic acid molecule is provided, wherein said molecule is a nucleic acid sequence selected from the group consisting of SEQ ID No. 1, SEQ ID No. 2, SEQ ID No. 3, SEQ ID No. 4, SEQ ID No. 5, SEQ ID No. 6, and SEQ ID No. 7, or comprising an amino acid sequence which is at least 60% sequence identical over the entire length of the sequence with SEQ ID No. 3, SEQ ID No. 4, SEQ ID No. 5, SEQ ID No. 6, and SEQ ID No. 7, respectively.

According to another embodiment of the eight aspect, a nucleic acid molecule is provided, wherein the nucleic acid molecule comprises SEQ ID No. 9 or a sequence that is at least 80% sequence identical over the entire length of the sequence with SEQ ID No. 9.

According to a ninth aspect, an expression vector is provided comprising a nucleic acid molecule encoding an isolated DNA polymerase derived 3'-5'exonuclease or an enzymatically active fragment thereof according to any of the aspects 1-14 and the necessary regulatory sequences for the transcription and translation of the protein sequence encoded by said nucleic acid molecule.

Said expression vector may according to one embodiment comprises a nucleic acid sequence selected from the group consisting of SEQ ID No. 1, SEQ ID No. 2, SEQ ID No. 3, SEQ ID No. 4, SEQ ID No. 5, SEQ ID No. 6, and SEQ ID No. 7 or comprising an amino acid sequence which is at least 60% sequence identical over the entire length of the sequence with SEQ ID No. 3, SEQ ID No. 4, SEQ ID No. 5, SEQ ID No. 6, and SEQ ID No. 7, respectively.

According to a tenth aspect, a host cell is provided comprising one or more expression vectors according to the present invention or one or more nucleic acid molecules according to the present invention.

According to an eleventh aspect, a method for preparation of a DNA polymerase derived 3'-5'exonuclease of the present invention or an enzymatically active fragment thereof is provided, comprising the steps of:
a) culturing a host cell comprising one or more of the recombinant expressions vectors according to anyone of the aspects 19 to 20 or one or more nucleic acid molecules according to anyone of the aspects 16 to 18 under conditions suitable for the expression of the encoded DNA polymerase;
b) isolating or obtaining the DNA polymerase derived 3'-5' exonuclease from the host cell or from the culture medium or supernatant.

According to a twelfth aspect, the present invention furthermore relates to the use of a DNA polymerase derived 3'-5'exonuclease of the invention or an enzymatically active fragment thereof in a recombinant cloning processes, wherein said exonuclease or an enzymatically active fragment thereof provides single stranded DNA overhangs of double stranded DNA molecules.

According to a thirteenth aspect, a method for removing contaminating polynucleotides from a sample is provided, said method comprising contacting the sample with DNA polymerase derived 3'-5'exonuclease of the invention or an enzymatically active fragment thereof.

According to a fourteenth aspect, a method for deleting a segment of one or more target double stranded nucleic acid molecules is provided, the method comprising contacting one or more double stranded nucleic acid molecules and a DNA polymerase derived 3'-5'exonuclease of the present invention or an enzymatically active fragment thereof, wherein said exonuclease cleaves nucleotides in 3'-5' direction of the double stranded nucleic acid molecules to produce complementary single stranded 5' overhangs.

According to a fifteenth aspect, a method for assembly of two or more double stranded (ds) DNA molecules are provided, said method comprising the steps of:

(a) providing two or more dsDNA molecules to be assembled, wherein the ends of the dsDNA molecules share a region of sequence identity;

(b) contacting the provided two or more DNA molecules with a heat labile DNA polymerase derived 3'-5' according the invention or an enzymatically active fragment thereof, whereby single stranded overhangs are generated in both ends of the provided dsDNA molecules;

(c) incubating the DNA molecules of (a) under conditions whereby said DNA molecules anneal through the overhang portions generated in step (b);

(d) optionally contacting the annealed molecules provided in step (c) with a DNA polymerase and allow the DNA polymerase to fill in the gaps, wherein said DNA polymerase have reduced, impaired or inactivated strand displacement activity.

According to one embodiment of the fifteenth aspect, the steps (a)-(d) is carried out at constant temperature.

According to another embodiment of the fifteenth aspect, the steps (a)-(d) is carried out at a temperature within the range of 18° C. to 25° C.

According to another embodiment of the fifteenth aspect, the assembled DNA molecule of step (c) or (d) is further transferred into a suitable host cell for propagation.

According to yet another embodiment of the fifteenth aspect step (b) is carried out at within a temperature within the range of 18° C. to 25° C. for about 5-15 minutes.

According to an embodiment of the above fourteenth and fifteenth aspects, digesting the dsDNA molecules or ds nucleic acid molecules, the length of the generated overhangs is from 10 to 40 nucleotides.

According to a sixteenth aspect, a process is provided for inserting at least one target double stranded nucleic acid molecule into an acceptor nucleic acid molecule to provide a recombinant double stranded nucleic acid molecule, comprising the steps:

(a) contacting a DNA polymerase derived 3'-5'exonuclease of the present invention or an enzymatically active fragment thereof and a target double stranded nucleic acid molecule, wherein said exonuclease cleaves nucleotides in 3'-5' direction of the ends of the target stranded nucleic acid molecules to produce complementary single stranded 5' overhangs;

(b) contacting a DNA polymerase derived 3'-5'exonuclease according to the present invention or an enzymatically active fragment thereof and a double stranded acceptor nucleic acid molecule, wherein said exonuclease cleaves nucleotides in 3'-5' direction of the ends of said acceptor nucleic acid molecule to produce complementary single stranded 5' overhangs;

(c) providing a reaction mixture comprising the product of steps (a) and (b), a DNA polymerase, oligonucleotide primer(s) which is capable of annealing to a portion of the nucleic acid molecule acid molecules of (a) and (b), and nucleotides;

(d) incubating said reaction mixture under conditions whereby the oligonucleotide primer anneals to the nucleic acid molecules of step (a) and (b), and whereby the DNA polymerase extends said oligonucleotide primer by polymerizing one or more nucleotides to produce a recombinant double stranded molecule.

According to one embodiment of the sixteenth aspect, the double stranded acceptor nucleic acid molecule is a vector. According to yet another embodiment of the sixteenth aspect, the steps (a) and (b) is performed at temperature within the range of 18° C. to 25° C. According to yet another embodiment of the sixteenth aspect, the DNA polymerase of step (d) is a heat labile DNA polymerase.

FIGURES

FIG. 2 shows the DNA and amino acid sequence of the enzyme of the present invention.

DETAILED DESCRIPTION OF THE INVENTION

Figure 1:
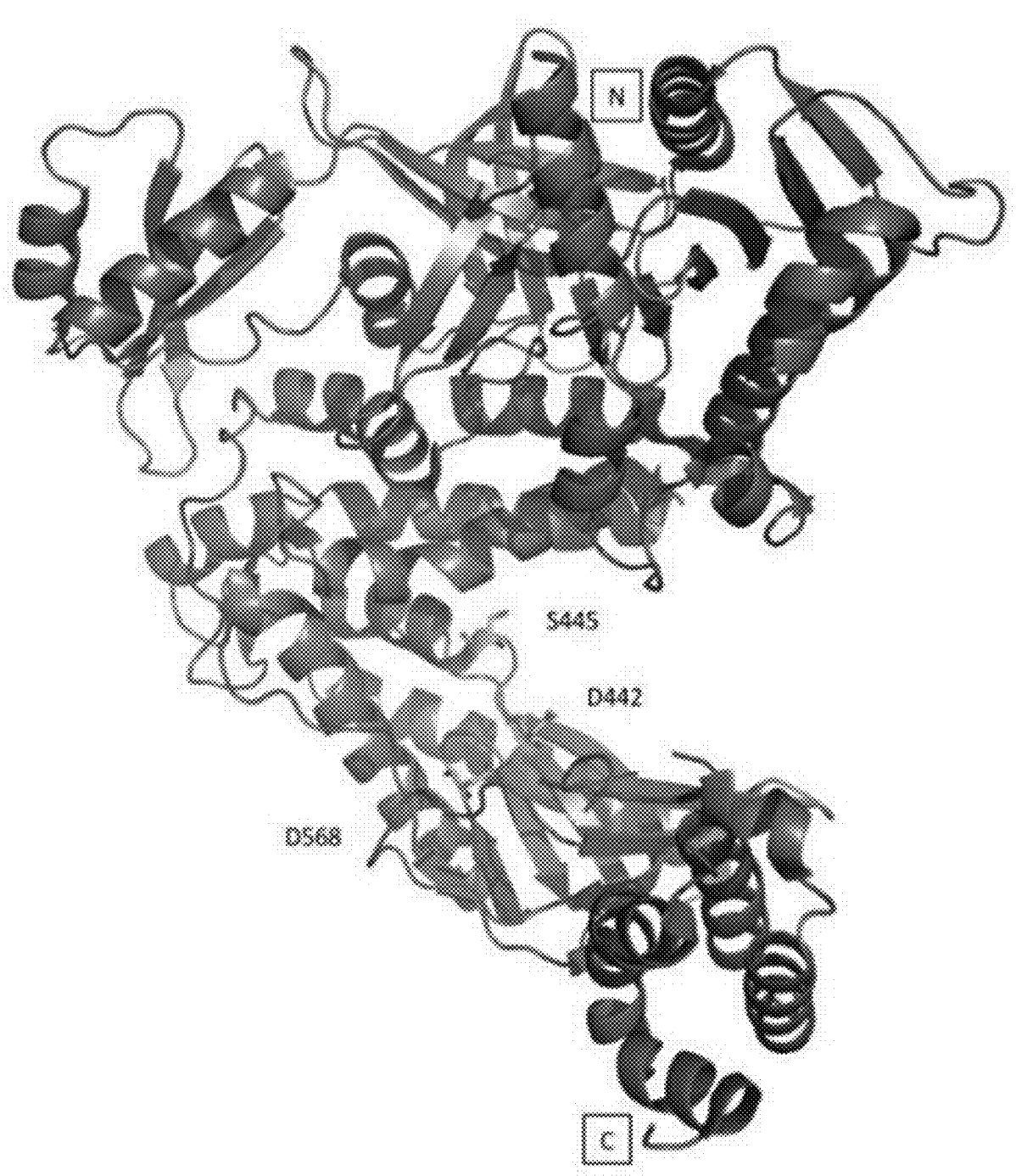
FIG. 1 represents a model of DNA polymerase II from *E. coli* (PDB code: 1Q8I), a homologous protein to DNA polymerase II from *M. viscosa* and illustrates the position of the amino acids D442, S445 and D568, as well as the C- and N-terminal end.

The present inventors have as mentioned identified a novel heat labile DNA polymerase of marine origin having a 3'-5' exonuclease activity and very poor polymerase activity, rendering said enzyme applicable in inter alia molecular cloning processes.

Throughout the present application, when referring to the "enzyme of the present invention", or "DNA polymerase derived 3'-5'exonuclease", it is to be understood that reference is made to the enzyme of the present invention, such as disclosed in the appended claims and described in the specification below. E.g. an enzyme comprising SEQ ID NO 2 or enzymatically active fragments thereof, or sequences having about 60% sequence identity over the entire sequence compared with SEQ ID No. 2. Said terms also includes enzymes that are modified compared with the isolated enzyme having an amino acid sequence of SEQ ID No. 2, e.g. by site directed mutagenesis, wherein the modified enzymes retain the enzymes 3'-5' exonuclease activity but have impaired, reduced or are lacking the DNA polymerase activity compared with the disclosed wild type DNA polymerase identified in *M. viscosa*.

As will be shown further below, the exonuclease activity may be used in order to provide target DNA molecules with 5'-3 overhang that can be easily inserted into a vector for amplification or expression of the target DNA molecule. It may also be used in polynucleotide removal processes, e.g.

in methods involving purification of proteins or other material where excess of or remnants polynucleotides are undesired.

Due to that the enzyme is heat labile and thus easily inactivated at temperatures above 25° C., such as at temperatures above about 30° C., the enzyme can be used at room temperature and also without the need of laboring or extra inactivation steps.

The enzyme of the present invention may be used in various processes carried out at room temperature. The term "room temperature" is a recognized term in the art and includes temperatures in within the range of 18° C. to 25° C.

The enzyme is found to be active for the time needed to remove contaminated DNA or form 5' overhang That is, upon contacting the target dsDNA with an enzyme of the present invention, overhangs of a length of about 10-40 nucleotides will be prepared before the enzyme stops digesting on the target DNA molecule due to its heat lability also at room temperatures. E.g. at room temperature, it is found that the enzyme form 5'overhang of dsDNA molecules having a length of about 10-40 nucleotides within approx. 5-30 minutes. If used to remove contaminating nucleic acids in purification process, the time needed may also vary dependent upon the type of sample to be purified and the amount of contaminating nucleic acids.

Unless specifically defined herein, all technical and scientific terms used have the same meaning as commonly understood by a skilled artisan in the fields of genetics, biochemistry, and molecular biology.

All methods and materials similar or equivalent to those described herein can be used in the practice or testing of the present invention, with suitable methods and materials being described herein. All publications, patent applications, patents and other references mentioned herein are incorporated by reference in their entirety. In case of conflict, the present specification, including definitions, will prevail.

Where a numeric limit or range is stated, the endpoints are included. Also, all values and sub ranges within a numerical limit or range are specifically included as if explicitly written out.

According to a first aspect, a DNA polymerase or an enzymatically active fragment thereof is provided that are irreversible inactivated at temperatures above about 30° C.

The expression "an enzymatically active fragment" of the DNA polymerase is to be understood to mean a DNA polymerase where the activity of the polymerase is maintained, that is having the same or at least similar activity compared with a DNA polymerases having an amino acid sequence as depicted in SEQ ID No. 1-8, although one or more amino acids are removed compared with the sequences depicted in SEQ ID No. 1-8. The skilled person will acknowledge that one or more amino acid may be removed, e.g. in the C- or N-terminal end of an amino acid sequence, without affecting the activity of the protein.

According to another aspect, a DNA polymerase derived 3'-5' exonuclease is provided, wherein said enzyme is substantially without polymerase activity, and furthermore is irreversibly inactivated at temperatures above 25° C., such as at temperatures above about 30° C.

According to a second aspect, a DNA polymerase or an enzymatically active fragment thereof is provided, comprising the amino acid sequence of SEQ ID No. 1 or SEQ ID NO. 2, or comprising an amino acid sequence which is at least 60% sequence identical over the entire length of the sequence with SEQ ID No. 1.

The present invention provides as mentioned a DNA polymerase having a 3'-5' exonuclease activity, or an enzymatically active fragment therefore, wherein said enzyme is substantially without polymerase activity. Variants of the wild type enzyme with reduced polymerase activity have been obtained using site directed mutagenesis.

In Blasco et al., The Journal of Biological Chemistry, vol 268, No. 32, pp 24106-24113, site directed mutagenesis was used to study the effect on the activity of small (66 kDa) single subunit DNA polymerase, suggesting that the motive Dx2SLYP formed part of the active site of the polymerase activity.

The expression "substantially without polymerase activity" is to be understood to mean that the active site of the polymerase activity of the enzyme of the invention is impaired or absent compared with the wild type DNA polymerase, said wild type DNA polymerase having an amino acid sequence according to SEQ ID No. 2. For example, the skilled person will acknowledge that a DNA polymerase having a polymerase activity that is reduced similar with the polymerase activity of a DNA polymerase derived 3'-5' exonucleases having an amino acid sequence of SEQ ID NO. 3-7 has an impaired polymerase activity, i.e. that are substantially without polymerase activity. The skilled person will furthermore acknowledge that polymerase activity can be measured using a real time molecular beacon assay, such as disclosed in Summerer, *Methods Mol. Biol.*, 2008, 429, 225-235 or in modified form as shown in example 4 below.

According to yet another aspect, the present invention provides an enzyme or an enzymatically active fragment thereof comprising an amino acid sequence of SEQ ID No. 1 or amino acid sequences that are at least 60% sequence identical over the entire length of the sequence with SEQ ID No. 1.

According to yet another aspect, the present invention provides an enzyme or an enzymatically active fragment thereof comprising an amino acid sequence of SEQ ID No. 2 or amino acid sequences that are at least 60% sequence identical over the entire length of the sequence with SEQ ID No. 2.

As mentioned above, a DNA polymerase is provided comprising an amino acid according to SEQ ID No. 1 or SEQ ID No. 2 and comprising at least one mutation in the regions corresponding to the amino acid positions G447-L453 and G519-A523 compared with the wild type sequence (SEQ ID No. 2).

The skilled person will acknowledge that amino acids are grouped dependent upon the chemical characteristics of the side chain. Amino acids are commonly classified as hydrophobic or hydrophilic and/or as having polar or non-polar side chain. Substitutions of one amino acid for another having the same biochemical characteristics are commonly known as conservative substitution. The skilled person will acknowledge that conservative substitutions can be introduced into an amino acid sequence of a protein, e.g. to the enzyme according to the present invention without altering the activity of said enzyme. Such modifications will thus be expected to constitute a biologically equivalent product.

Conservative substitution of amino acids include substitution made among amino acids within the following groups:

Val, Ile, Leu, Met (amino acids with hydrophobic side chain)

Phe, Tyr, Trp (amino acids with hydrophobic side chain)

Arg, His, Lys (amino acids with positively charged side chain)

Ala, Gly (amino acids with small side chain)

Ser, Thr (amino acids with uncharged side chains)

Asn, Gln (amino acids with uncharged side chains)

Asp, Glu (amino acids with negative charged side chain)

Generally, a conservative amino acid substitution refers to an amino acid substitution that does not alter the relative charge or size characteristics of the protein in which the amino acid substitution is made, and thus seldom alter the three-dimensional structure of the protein, which is why the biological activity are neither altered significantly.

The skilled person will thus acknowledge that an enzyme having an amino acid sequence according to SEQ ID No. 1 or SEQ ID No. 2, wherein the amino acid in position 442 is selected from the group consisting of Asp, Glu, Ala, Gly, Val, Leu, Ile and/or the amino acid in position 445 is selected from the group consisting to Ser, Thr, Arg, His, Lys, and/or wherein the amino acid in position 568 is selected from the group consisting of Asp, Glu, Ala, Gly, Val, Leu, Ile, provided that the amino acids in position 442 (D442), 445 (S445), and 568 (D568) is not Asp, Ser, and Asp, respectively, will have the same or approximately the same polymerase activity and 3'-5' exonuclease activity as an enzyme according to SEQ ID NO. 3-8.

Also, the skilled person will understand that one or more amino acids may be deleted, inserted or added without altering the activity of the enzyme of the present invention.

It is thus to be understood that the present invention encompasses DNA polymerase derived exonucleases as disclosed in the appended claims, wherein such modifications as described above (substitutions, deletions, insertions and additions of amino acids) may be introduced without essentially altering the activity of the enzyme, i.e. in respect of polymerase activity and exonuclease activity.

According to yet another aspect, the present invention provides a DNA-polymerase or an enzymatically active fragment thereof comprising an amino acid sequence selected from the group consisting of SEQ ID No. 3, 4, 5, 6, 7 and 8, or comprising an amino acid sequence which is at least 60% sequence identical over the entire length of the sequence with SEQ ID No. 3, 4, 5, 6, 7 and 8, respectively.

According to another aspect, an enzyme is provided comprising an amino acid sequence having at least 60% sequence identity over the entire length of the sequence, such as at least 70%, such as at least 75%, such as at least 80%, such as at least 85% such as at least 90%, such as at least 95%, such as at least 97%, such as at least 98% or 99% sequence identity with an amino acid sequence selected from the group consisting of SEQ ID No. 1, SEQ ID No. 2, SEQ ID No. 3, SEQ ID No. 4, SEQ ID No. 5, SEQ ID No. 6, 7 and SEQ ID No. 8.

Furthermore, the present invention also provides a nucleic acid molecule encoding an enzyme according to the present invention or an enzymatically active fragment thereof, as well as nucleic acid molecules being substantially homologous thereto.

According to one aspect, a nucleic acid molecule is provided encoding an amino acid sequence selected from the group consisting of SEQ ID No. 1, SEQ ID No. 2, SEQ ID No. 3, SEQ ID No. 4, SEQ ID No. 5, SEQ ID No. 6, and SEQ ID No. 7 or comprising an amino acid sequence which is at least 60% sequence identical over the entire length of the sequence with SEQ ID No. 3, SEQ ID No. 4, SEQ ID No. 5, SEQ ID No. 6, 7 and SEQ ID No. 8, respectively.

According to yet another aspect, a nucleic acid molecule is provided comprising the sequence as depicted in SEQ ID No. 9 or nucleic acid molecules which is at least 80% sequence identical over the entire length of the sequence with SEQ ID No. 9, such as at least 85%, such as at least 90%, such as at least 95%, such as at least 97%, such as at least 98%, such as at least 99% sequence identical over the entire length of the sequence with SEQ ID No. 9.

The skilled person will thus acknowledge that a DNA polymerase having an amino acid sequence according to SEQ ID No. 1 or SEQ ID No. 2, wherein the amino acid in position 442 is selected from the group consisting of Glu, Asp, Ala, Gly, Val, Leu, and Ile and/or the amino acid in position 445 is selected from the group consisting to Ser, Arg, Lys, and His, and/or wherein the amino acid in position 568 is selected from the group consisting of Glu, Asp, Ala, Gly, Val, Leu, and Ile may have the same or approximately the same 3'-5 exonuclease activity and reduced or inactivated polymerase activity as a DNA polymerase according to SEQ ID NO. 3-8.

Also, the skilled person will understand that one or more amino acids may be deleted, inserted or added without altering the activity of the enzyme of the present invention.

It is thus to be understood that the present invention encompasses DNA polymerases as disclosed in the appended claims, wherein such modifications as described above (substitutions, deletions, insertions and additions of amino acids) may be introduced without essentially altering the activity of the enzyme, i.e. according to the present invention in respect of 3'-5 exonuclease activity.

As used herein, both in respect of proteins and nucleic acid molecules or fragment thereof, when referring to "sequence identity", a sequence having at least x % identity to a second sequence means that x % represents the number of amino acids in the first sequence which are identical to their matched amino acids of the second sequence when both sequences are optimally aligned via a global alignment, relative to the total length of the second amino acid sequence. Both sequences are optimally aligned when x is maximum. The alignment and the determination of the percentage of identity may be carried out manually or automatically. Whenever referring to sequence identity herein, it is to be understood that the comparison is made with the entire sequence depicted in SEQ ID NO. 1-SEQ ID No. 9, respectively.

The skilled person will acknowledge that alignment for purposes of determining percent amino acid sequence identity can be achieved in various ways that are within the skill in the art, for instance, using publicly available computer software such as ClustalOmega (Sievers F, Higgins D G (2018) *Protein Sci* 27:135-145), Protein BLAST (from National Center for Biotechnology Information (NCBI), USA) or commercially available software such as Megalign (DNASTAR) software. Those skilled in the art can determine appropriate parameters for measuring alignment, including any algorithms needed to achieve maximal alignment over the full length of the sequences being compared. NCBI BLAST is another example of software used to determine amino acid sequence identity (MacWilliam et al., *Nucleic Acids Res.* 2013 July; 41(Web Server issue): W597-W600).

The skilled person will acknowledge that modifications may be introduced in a nucleic acid molecule which does not alter the amino acid sequence, e.g. the substitution of a nucleotide resulting in that the triplet affected by the substitution still codes for the same amino acid. For example, the amino acid isoleucine is encoded by the triplets (DNA codons) ATT, ATC, and ATA. Following, a substitution in the third nucleotide in the isoleucine triplet ATT from T to C or A, will not alter the resulting amino acid sequence. Such nucleotide modifications may be introduced by techniques well known to the skilled person (e.g. site directed mutagenesis) to adapt the nucleic acid sequence to the codons preferably used by a host cell and thus to enhance the expression of the enzyme.

Furthermore, nucleic acid molecules coding polypeptides which facilitates isolation and purification can be added to the nucleotide sequences of the present invention without affecting the activity of the resulting enzyme.

Also, nucleic acid molecules coding signal peptide providing for secretion of the desired enzyme from a host cell may also be linked to the nucleic acid sequences of the present invention.

The present invention furthermore comprises compositions comprising the DNA-polymerase derived 3'5' exonuclease of the present invention or enzymatically active fragments thereof. The composition may furthermore comprise a buffer. The skilled person will acknowledge that buffers used in composition comprising an enzyme of the invention may vary and optimised according to the enzyme of choice and the process wherein the enzyme is used. The 3'-5' exonuclease activity of the enzymes of the present invention is retained within the conditions commonly used in molecular cloning, DNA assembly and polynucleotide digestion methods well known to the skilled person, that is e.g. in respect of type and concentration of salt(s), pH conditions, etc.

For example, well known buffers such as Tris buffer may be used, such as a Tris buffer having a pH above about 8.0, for example a pH within the range of 8.0 and 9.0. According to one aspect, the pH of the composition is within 8.5-9.0.

Furthermore, the skilled person will acknowledge that the type of salts and concentration thereof may vary. According to one aspect, the composition comprises one or more salts selected from the group consisting of NaCl and KCl. According to another aspect of the present composition comprises NaCl and KCl. According to yet another aspect, the composition comprises up to about 25 mM NaCl and KCl.

Preparation of the DNA Polymerase of the Present Invention

The enzyme of the present invention and the enzymatically active fragments thereof or the nucleic acid molecule encoding them, is purified from or isolated from their natural environment or they are produced by cloning procedures and recombinant DNA procedures well known to the skilled person.

Nucleic acid molecules encoding a DNA polymerase derived 3'-5' exonuclease according to the present invention or encoding an enzymatically active fragment thereof may synthesized by methods well known to the skilled person or commercial suppliers, such as e.g. Genscript, Thermo Fisher Scientific etc.

The skilled person is well aware and familiar with the various available biotechnological techniques for expression of isolated or purified nucleic acid molecules for preparation of recombinant proteins by heterologous expression in various host cell systems using commonly available genetic engineering techniques and recombinant DNA expression systems, cf. e.g. "Recombinant Gene Expression Protocols, in Methods in Molecular Biology, 1997, Ed. Rocky S Tuan, Human Press (ISSN 1064-3745) or Sambrook et al., Molecular Cloning: A laboratory Manual (third edition), 2001, CSHL Press, (ISBN 978-087969577-4). For example, the nucleic acid molecule encoding the enzymes according to the present invention or encoding an enzymatically active fragment thereof may be inserted in a suitable expression vector comprising all the necessary transcriptional and translational regulatory sequences specifically adapted for directing the expression of the desired protein coding nucleic acid sequence in a suitable host cell. Suitable expression vectors are e.g. plasmids, cosmids, viruses or artificial yeast chromosomes (YAC's).

For example, DNA molecules to be expressed and used to prepare a DNA polymerase according to the present invention may be inserted into vectors used for propagation of the sequence of interest or for expression of the DNA polymerase encoding sequence of the invention. FastCloning is an example of an applicable method for this purpose.

According to one aspect of the invention, a vector, such as an expression vector, is provided comprising a nucleic acid molecule encoding an enzyme according to the present invention or an enzymatically active fragment thereof.

According to a further aspect, a vector, such as an expression vector is provided comprising a nucleic acid molecule encoding an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, and SEQ ID No. 8, or amino acid sequences having at least about 60% sequence identity over the entire length of the sequence. such as at least, 70%, 75%, 80%, 85%, 90%, 95%, 96%, 97%, 98%, or 99% sequence identity over the entire length of the sequence of SEQ ID No. 1, SEQ ID No. 2, SEQ ID No. 3, SEQ ID No. 4, SEQ ID No. 5, SEQ ID No. 6, 7 and SEQ ID No. 8.

According to yet another aspect, a vector is provided comprising SEQ ID No. 9 or a sequence with 80% sequence identity over the entire length of the sequence of SEQ ID No. 9, such as at least, 85%, 90%, 95%, 96%, 97%, 98%, or 99% sequence identity over the entire length of the sequence of SEQ ID No. 9.

The skilled person will acknowledge that a DNA polymerase according to the present invention may be prepared using an expression vector comprising a nucleic acid molecule encoding a DNA polymerase according to the present invention, wherein said molecule is operably linked to a promotor adapted for the host cell in question.

The skilled person will furthermore acknowledge that a "promoter" as used herein refers to a region of DNA upstream (5') of a DNA coding sequence that controls and initiates transcription of the particular gene. The promoter controls recognition and binding of RNA polymerase and other proteins to initiate transcription. "Operably linked" refers to a functional linkage between a promoter and a second sequence, where the promoter sequence initiates and mediates transcription of the DNA sequence corresponding to the second sequence. In general, operably linked means that the nucleic acid sequences being linked are contiguous. For example, a vector adapted for expression of recombinant proteins in bacterial host cells may comprise a promotor applicable for bacterial expression systems, such as the T7 promoter.

A vector according to the present invention, may be isolated using standard plasmid isolation techniques well known to the skilled person, such as e.g. using a QIAprep™ Spin Miniprep kit from Qiagen™ or QIAGEN™ Plasmid Plus Maxi Kit.

The expression vector including the nucleic acid molecule encoding an enzyme of the present invention or an enzymatically active fragment thereof may be introduced in suitable host cells for the production of the desired enzyme. According to one aspect of the invention, a host cell is provided comprising a vector of the invention, comprising a nucleic acid molecule encoding the desired enzyme.

Various commercial available host cells or viruses may be used. For example, bacterial host cells may be used, such as E. coli, CL21 cells, or Rosetta 2 (DE3) cells (Novagen). Transformation of the expression vector may be performed by methods well known to the skilled person, e.g. using chemically competent cells.

Upon culturing the host cells in a suitable culturing media, the enzyme of the present invention or an enzymatically active fragment thereof encoded by the expression vector in the host cell will be produced, and the resulting enzyme may be collected and purified by methods well known to the skilled person.

The expression vector may furthermore include signal sequences for secretion of the expressed enzyme into the culture media.

As outlined above, the enzyme of the present invention may be synthesized using recombinant DNA technology. Alternatively, the enzyme of the present invention is prepared using cell-free expression systems, or it may be manufactured using chemical peptide synthesis methods, e.g. by stepwise condensation reaction of the carboxyl group of one amino acid to the amino group of another in accordance with the desired sequence of amino acids.

According to one aspect, a process for the preparation of an enzyme of the present invention or a enzymatically active fragment thereof is provided, comprising the steps of (i) culturing a host cell comprising one or more expression vectors of the present invention suitable for the expression of the encoded enzyme; and optionally (ii) isolating or obtaining the enzyme from the host cell or from the culture medium (supernatant).

The skilled person will acknowledge that various methods are available for isolating and optionally purifying a recombinant expressed protein from a host cell or a culture medium. For isolation and purification of the obtained expressed enzyme from the fermentation broth, one or more pre-treatments or clarification steps is commonly used first in order to remove large particles and biomass. Non-limiting examples of applicable pre-treatment steps are e.g. reverse osmosis, centrifugation, filtration methods and diafiltration, or a combination thereof. The obtained enzyme is then commonly purified by one or more of a variety of chromatographic methods well known to the skilled person, e.g. by affinity chromatography, ion-exchange chromatography, mixed-mode chromatography, hydrophobic interaction chromatography, size exclusion chromatography or other chromatography techniques, or a combination thereof.

For example, an enzyme expressed by a suitable host cell may be purified using an affinity chromatography method, such as using MabSelect™ SuRe™ media and a HiTrap MabSelect™ SuRe™ column mounted on an FPLC chromatography system, e.g. the BioRad NGC Discover™ 10 Pro system fitted with a 5 mm UV flow cell. After loading of the sample comprising the enzyme to be purified, the column is commonly washed one or more times with one or more applicable wash buffers, where after the protein is eluted using an applicable elution buffer. The obtained enzyme may be further purified using one or more of the chromatography methods listed above.

Use of the DNA Polymerase Derived 3'-5' Exonuclease of the Invention.

The present enzyme may be used in any process, where it is desired to provide an overhang of the ends of a dsDNA molecule. In particular, the present enzyme is applicable in processes where it is desirable to provide overhangs of a length within 10 to 40 nucleotides, and wherein the process is carried out at a temperature in the range of 18° C. to 25° C.

Various methods based on homolog recombination techniques are known for assembly of nucleic acid molecules. The present enzyme is particularly useful in methods for assembly of nucleic acid molecules based on homologue recombination, and in particular methods adapted for assembly of a large number of nucleic acid molecules, wherein the ends of the dsDNA molecules to be assembled share a region of sequence identity and the exonuclease of the invention is used to provide overhang prior to assembly of the DNA molecules.

For example, the enzyme of the invention or enzymatically active fragments thereof may be used in the method disclosed in WO2007/124065. WO2007/124065 disclose an in vitro homologous recombination method that are sequence and ligase independent (SLIC), wherein dsDNA molecules are assembled by combining exonuclease treated target DNAs with homologous overhangs that are annealed, and wherein the missing nucleotides in the annealed region is filled in by the appropriate host cell after transformation.

Reference is also made to Gene Synthesis, Methods and Protocols, Methods in Molecular biology, 2012, vol. 852, pp 51-59 disclosing a SLIC protocol for production of recombinant DNA wherein target dsDNA(s) is inserted into a vector of choice using the exonuclease activity of T4 DNA polymerase (in absence of dNTPs) to produce single stranded overhangs of the dsDNA to be combined, followed by annealing and ligase treatment of the annealed product.

Other methods based on homolog recombination is presented in e.g. EP1929012 disclosing a homologue recombination method wherein dsDNA molecules are assembled after being treated with a 3'-5' exonuclease that produces overhang, followed by annealing, contacting the annealed products with a DNA polymerase, and finally sealing the remining nicks using a ligase, and wherein the process is performed in the presence of a crowding agent (such as PEG).

The present DNA polymerase may also be used in other similar methods, such as the methods disclosed in EP1915446A1 and EP2255013.

Multiple DNA assembly systems are also commercial available, such as e.g. GeneArt® assembly products provided by ThermoFisher Scientific and the NEB Gibson Assembly®, NEBuilder® HiFi DNA Assembly and Golden Gate Assembly offered by NewEngland Biolabs Inc.

Figure 2:
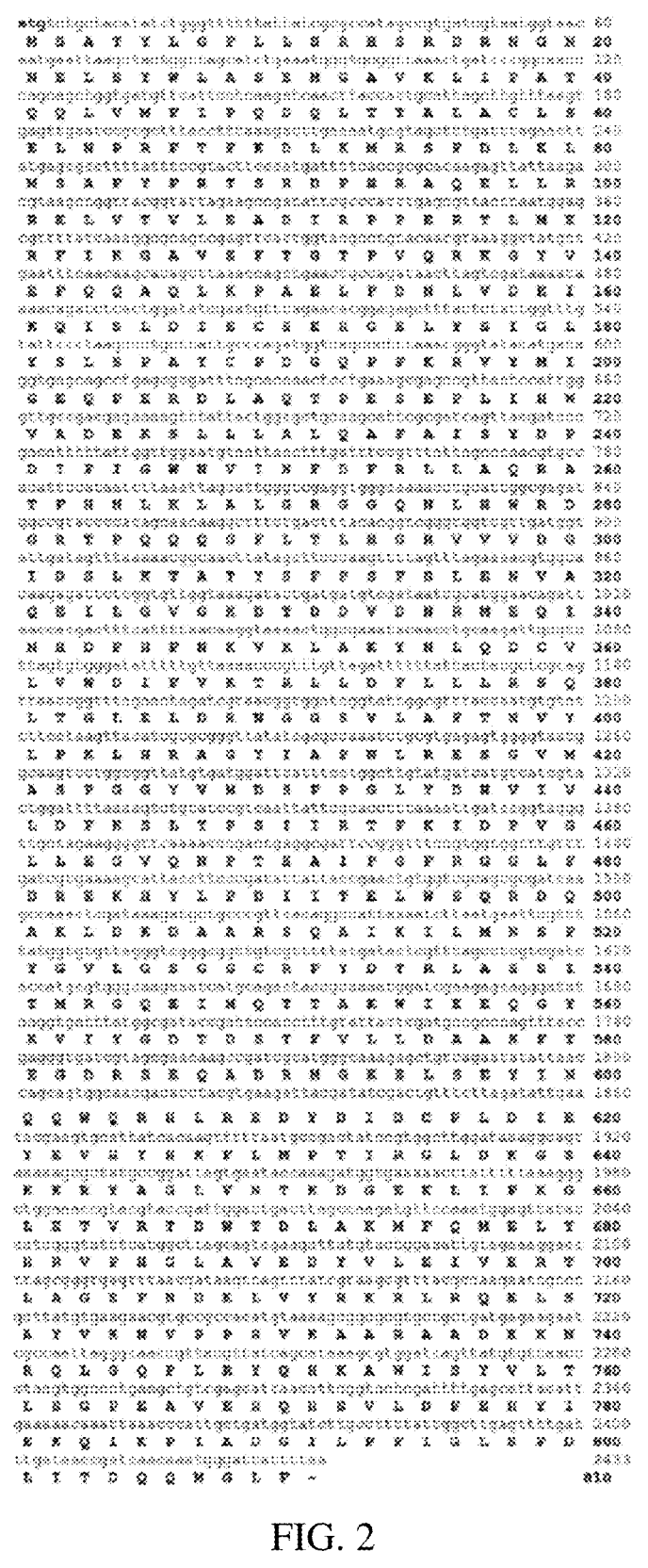

In order to assembly multiple DNA molecules in the desired order, the ends to be assembled should share sequence identity ensuring that the respective overhangs of in question resulting from the exonuclease digestion step anneals (hybridize). The length of the overhang is preferably of a length sufficient to hybridize specifically to complementary overhangs of the shared region of sequence identity, so as to allow hybridization of the single-stranded overhangs. As illustration of the principles of annealing multiple dsDNA molecules, reference is made to FIG. 2 page 54 in SLIC: a method for sequence and ligation independent cloning by Li and Elledge, 2012, Gene Synthesis, pp 51-59.

According to the present invention, the length of the overhangs prepared by contacting the dsDNA molecules to be assembled with the DNA polymerase derived 3'-5' exonuclease is 10-40 nucleotides.

According to one aspect, a process is provided, said process comprising the steps of:
    (a) providing two or more dsDNA molecules to be assembled, wherein the ends of the dsDNA molecules share a region of sequence identity; and wherein, for each pair of dsDNA molecules to be joined, the distal region of the first DNA molecule and the proximal region of the second DNA molecule share a region of sequence identity comprising from 10-40 nucleotides;

(b) contacting the provided two or more DNA molecules with a heat labile DNA polymerase derived 3'-5' exonuclease enzyme according to the invention, whereby single stranded overhangs are generated in both ends of the provided dsDNA molecules;

(c) incubating the DNA molecules of (a) under conditions whereby said DNA molecules anneal through the overhang portions generated in step (b);

(d) optionally contacting the annealed molecules provided in step (c) with a DNA polymerase and allow the DNA polymerase to fill in the gaps, wherein said DNA polymerase have reduced, impaired or inactivated strand displacement activity, and exert proof reading activity.

The enzyme of the present invention is particularly suitable due to that digestion of the dsDNA molecules of interest to provide single stranded overhangs can be carried out at room temperature. Furthermore, as the enzyme of the present invention is heat labile and inactivated at temperatures above 25° C., no laborious inactivation step is needed.

The present invention therefore provides methods for assembly of two or more double stranded (ds) DNA molecules as disclosed in the appended claims.

According to one embodiment, one of the at least two or more dsDNA molecules to be assembled in a multiple DNA assembly process of the invention is a vector. The vector and the dsDNA molecules to be assembled may be contacted with the DNA derived 3'-5' exonuclease of the present invention separately or together in one step.

The exonuclease activity of the present enzymes may also be used in methods for removing polynucleotides, e.g. in purification methods. For example, the enzyme may be used in purification of polypeptides or proteins isolated from natural sources or expressed in various host systems, wherein polynucleotides represent impurities or contaminants, and wherein incubation of a solution comprising the desired protein with the enzyme of the present invention provides a non-polynucleotide purified solution of the desired protein in question. Also, other solutions comprising one or more reagents of interest, contaminated with polynucleotides may be purified using the present enzyme. One advantage of the present invention when used removing polynucleotides from solutions comprising proteins or other reagents, is that the enzyme may be used at room temperature, and furthermore that no inactivation steps are necessary, thus avoiding e.g. addition of inactivation additives, such as metal ions or chelating agents, which may have an undesired effect on the protein or reagents in question or the further use thereof.

EXAMPLES

Example 1 Cloning of DNA Polymerase II Derived 3'-5' Exonuclease

Lunder et al. reported in Disease of Aquatic Organisms, vol. 23, No. 23, pp. 39-49 in 1995 experiments with a *Vibrio* like bacterium isolated from farmed Atlantic salmon affected by winter ulcer disease. Later, it was found that the isolated bacterium was a psychotrophic marine *M. viscosa* bacterium.

The providing of the gene encoding the enzyme of the present enzyme was obtained using the below primers in polymerase chain reaction using genomic DNA of said *M. viscosa* (GenBank: LN554852.1).

The identified gene encoding DNA polymerase I from *M. viscosa* was cloned into the pHMGWA vector using the Gateway® Technology (Thermo Fisher). Starting material for the polymerase chain reaction was the genomic DNA of *M. viscosa*. The various mutations were introduced using the QuikChange II Site-Directed Mutagenesis Kit (Agilent Technologies) and confirmed by sequencing analysis.

```
forward primer
                                 (SEQ ID NO. 10)
5'-CACCTTGTCTGCTACATATCTGGGT-3' reverse primer
                                 (SEQ ID NO. 11)
5'-TTAAAATAATCCCATTTGTTGATCGGTTATCA-3'
```

In order to provide modified enzymes, wherein the polymerase activity of the identified enzyme is reduced, impaired or inactivated compared with the wild type enzyme, various mutations were introduced in the identified cloned gene by QuikChange II Site-Directed Mutagenesis Kit (Agilent Technologies) and confirmed by sequencing analysis.

Example 2: Preparation of Recombinant Enzyme (MV Pol II and Mutants Thereof)

For expression of the enzymes of the present invention in host cells, gene sequences encoding the present DNA polymerase (SEQ ID No. 2, codon optimized for the host cells in question) was introduced in the Gateway Destination Vector pHMGWA.

Recombinant protein production of the enzyme according to the present invention was performed in Rosetta 2 (DE3) cells (Novagen®). The cells grew in Terrific Broth media/ampicillin (100 µg/ml) and gene expression was induced at $OD_{600}$ nm 1.0 by addition of 0.1 mM IPTG. Protein production was carried out at 15° C. for 6-8 h.

For protein purification the pellet of a 1-1 cultivation was resuspended in 50 mM HEPES pH 7.5 (at 25° C.), 500 mM NaCl, 5% glycerol, 0.15 mg/ml lysozyme, 1 protease inhibitor tablet (Complete™, Mini, EDTA-free Protease Inhibitor Cocktail, Roche) and incubated on ice for 30 min.

Cell disruption was performed by sonication with the VCX 750 from Sonics® (pulse 1.0/1.0, 15 min, amplitude 25%). In the first step, the soluble part of the His6-tagged protein present after centrifugation (48384 g, 45 min, 4° C.) and filtration (Ø 0.45 µm) was purified by immobilized $Ni^{2+}$-affinity chromatography. After a wash step with 50 mM HEPES (at 25° C.), 500 mM NaCl, 35 mM imidazole, 5% glycerol, the protein was eluted at an imidazole concentration of 250 mM and further transferred into 50 mM HEPES (at 25° C.), 500 mM NaCl, 10 mM $MgCl_2$, 5% glycerol by use of a desalting column. The second step was the cleavage of the tag by the TEV protease performed over night at 4° C. in 50 mM Tris pH 8.0, 0.5 mM EDTA and 1 mM DTT. To separate the protein from the His6-tag and the His6-tagged TEV protease a second $Ni^{2+}$-affinity chromatography has been performed in the third step by applying 50 mM HEPES (at 25° C.), 500 mM NaCl, 5% glycerol. The final protein solution was concentrated and stored with 50% glycerol at −20° C. for activity assays.

Example 3: Measuring of Polymerase Activity of the Present Enzyme

In order to measure the polymerase activity of the present enzyme and also compare said novel enzyme with known DNA polymerases, an assay based on a molecular beacon probe (modified from Summerer, *Methods Mol. Biol.,* 2008, 429, 225-235) was used. The molecular beacon template consists of a 23mer loop that is connected by a GC-rich 8mer stem region (sequence is indicated in italics) and a 43mer extension. Due to the loop formation the fluorophores Dabcyl and FAM are in close proximity and thus quenched. Upon extension by the DNA polymerase I of the primer that is annealed to the molecular beacon template the stem is opened and the increase in distance of the two fluorophores is measured by the restoration of FAM fluorescence (excitation 485 nm, emission 518 nm).

```
molecular beacon template
                                        (SEQ ID. NO. 12)
5'-GGCCCGT^Dabcyl AGGAGGAAAGGACATCTTCTAGCAT^FAM ACGGG

CCGTCA-AGTTCATGGCCAGTCAAGTCGTCAGAAATTTCGCACCA

C-3' primer
                                        (SEQ ID. NO. 13)
5'-GTGGTGCGAAATTTCTGAC-3'
```

The molecular beacon substrate was produced by incubating 20 μl of 10 μM molecular beacon template and 15 μM primer in 10 mM Tris-HCl pH 8.0, 100 mM NaCl for 5 min at 95° C. The reaction was then let to cool down at room temperature for 2 h. The substrate solution was stored at −20° C. with a final concentration of 10 μM.

Figure 3:
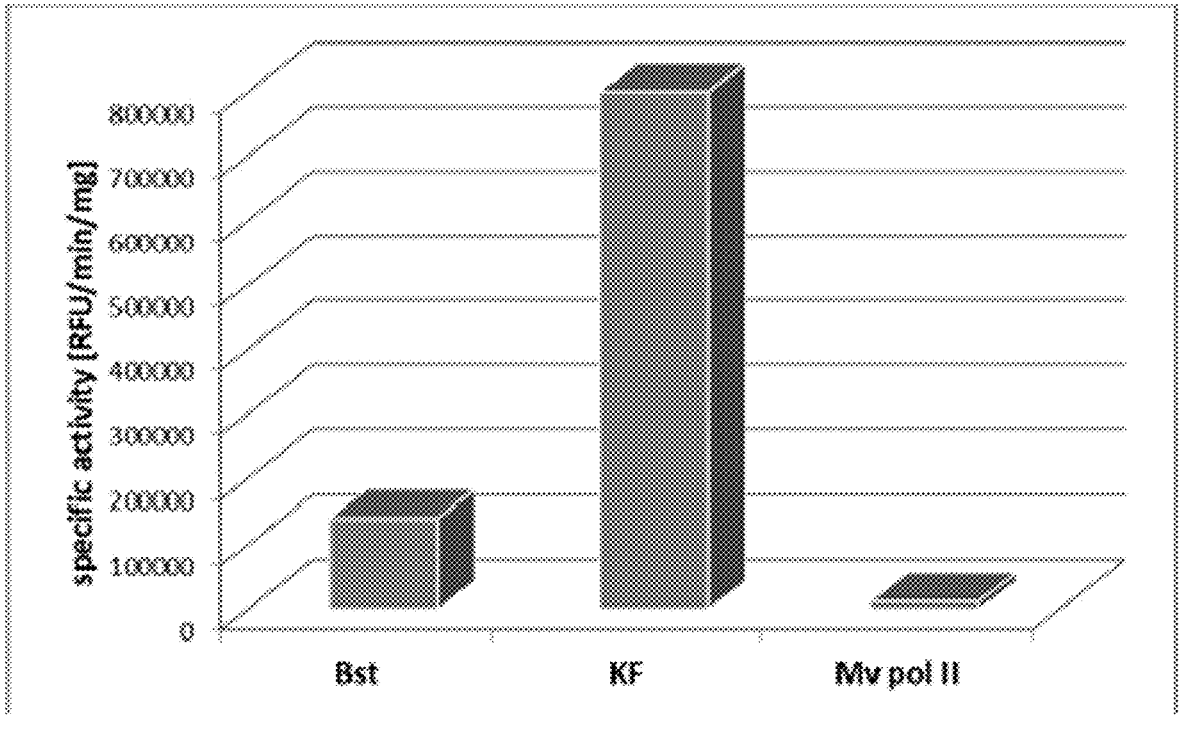
FIG. 3 shows the polymerase activity of the enzyme of the present invention (MV Pol II) compared with the polymerase activity of the Klenow fragment enzyme (KF) from *E. coli* and the thermophilic *Bacillus stearothermophilus* (Bst) polymerase.
Figure 4:
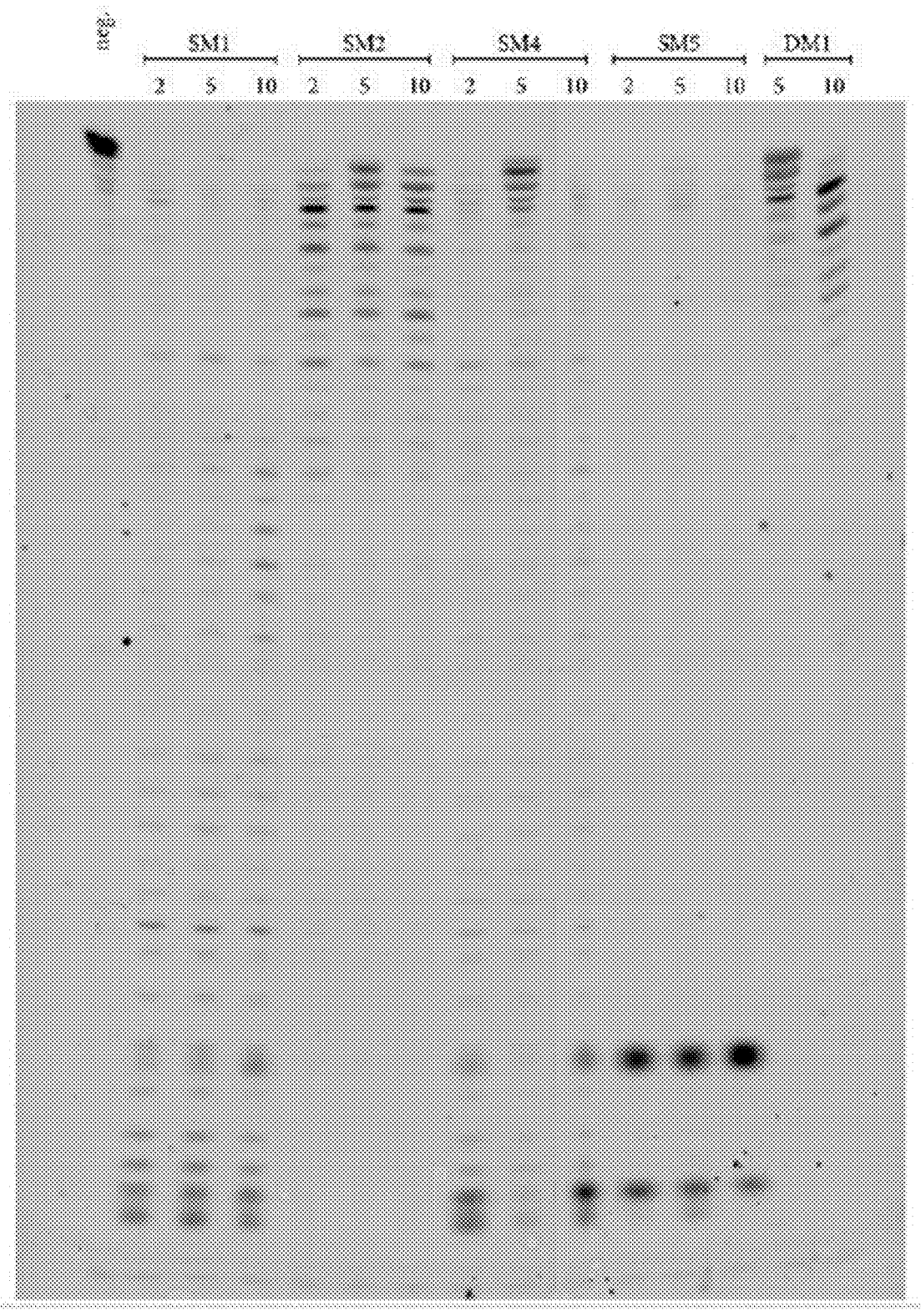
FIG. 4 shows exonuclease activity of DNA polymerases derived 3'-5' exonucleases of the present invention.
Figure 5:
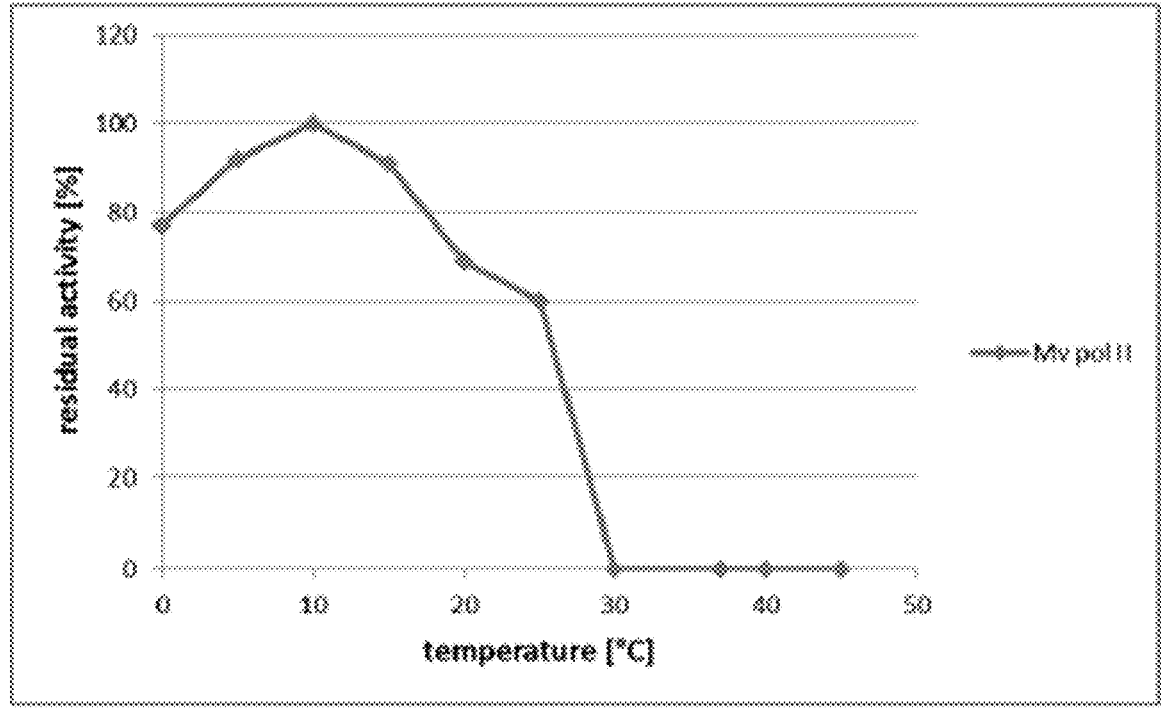
FIG. 5 shows the exonuclease activity of the isolated enzyme of the present invention (MV pol II) at various temperatures.

Fifty microliter reactions consisted of 200 nM substrate and 200 μM dNTP (equimolar amounts of dATP, dGTP, dCTP and dTTP). The reaction further contained 5 mM MgCl₂ in 50 mM Tris-HCl pH 8.5, 100 mM KCl, 1 mM DTT, 0.2 mg/ml BSA and 2% glycerol. The activity assay was carried out at 25° C. in black 96-well fluorescence assay plates (Corning®). The reaction was initiated by addition of protein solution, i.e. MV pol II and its variants. The increase in FAM fluorescence was measured as relative fluorescence units in appropriate time intervals by exciting at 485 nm and emission at 518 nm. The measurement was performed in a SpectraMax® Gemini Microplate Reader (Molecular Devices). The results are shown in FIG. 3 and shows that the enzyme of the present invention has a low DNA polymerase activity.

Example 5: 3'-5' Exonuclease Activity of the Present Enzyme

The blunt-ended dsDNA substrate for the exonuclease assay was produced by incubation of 40 μl 0.5 μM template DNA with 0.5 μM FAM-labeled reverse complementary strand (SEQ ID No, 14 and SEQ ID No. 15) in 10 mM Tris-HCl pH 8.0, 100 mM NaCl at 75° C. for 5 min. The reaction was then let to cool down at room temperature for 2 h. The substrate solution was stored at −20° C. with a final concentration of 0.5 μM.

Ten microliter reactions contained 25 nM substrate, 5 mM MgCl₂ in 50 mM Tris-HCl pH 8.0, 25 mM NaCl, 1 mM DTT, 0.2 mg/ml BSA and 2% glycerol. The reactions were initiated by addition of 0.02 μg/μl protein, i.e. MV pol II and its variants. As a negative control protein dilution buffer has been used instead of protein solution. Reactions were stopped by addition of 2.5 μl denaturing gel loading buffer (95% formamide, 10 mM EDTA, 0.1% xylene cyanol) and incubation at 95° C. for 5 minutes. For the denaturing polyacrylamide gel electrophoresis (12% polyacrylamide/7 M urea) a sample volume of 6 μl was loaded onto the gel. The gel electrophoresis was performed in 0.5× TBE buffer (44.5 mM Tris, 44.5 mM boric acid, 1 mM EDTA) at 50 W for 1 hour 15 minutes and the gel subsequently scanned with the PharosFX Plus Imager (Bio-Rad).

```
                                        (SEQ ID. NO. 14)
5'-[FAM]TATCCACCAATACTACCCTACGATACTTTGTCCACTCAAT-
3'

(SEQ ID. NO. 15)
3'-ATAGGTGGTTATGATGGGATGCTATGAAACAGGTGAGTTA-5'
```

Overview of the Sequence Numbers Referred to in the Specification and Sequence Listing

| SEQ ID No. | Sequence information |
|---|---|
| 1 | DNA polymerase derived 3'-5' exonuclease with variable amino acid positions 442, 445 and 568. |
| 2 | Wild type sequence of DNA polymerase derived 3'-5' exonuclease identified in *M. viscosa.* |
| 3 | DNA polymerase derived 3'-5' exonuclease wherein aspartate in position 442 is replace by alanine compared with the wild type sequence SEQ ID No. 2 (D442A, SM1) |
| 4 | DNA polymerase derived 3'-5' exonuclease wherein aspartate in position 568 is replaced by alanine compared with the wild type sequence SEQ ID No. 2 (D568A, SM2) |
| 5 | DNA polymerase derived 3'-5' exonuclease wherein aspartate in position 442 is replaced by glutamate compared with the wild type sequence SEQ ID No. 2 (D442E, SM4) |
| 6 | DNA polymerase derived 3'-5' exonuclease wherein aspartate in position 568 is replaced by glutamate compared with the wild type sequence SEQ ID No. 2 (D568E, SM5) |
| 7 | DNA polymerase derived 3'-5' exonuclease wherein aspartate in position 442 and 568 is replaced by alanine, respectively compared with the wild type sequence SEQ ID No. 2 (D442A/D568A, DM1) |
| 8 | DNA polymerase derived 3'-5' exonuclease wherein serine in position 445 is replaced by arginine compared with the wild type sequence SEQ ID No. 2 (S445R) |
| 9 | Nucleic acid sequence encoding a DNA polymerase comprising an amino acid sequence according to SEQ ID No. 2 |
| 10 | forward primer used in cloning of wild type DNA polymerase II gene |
| 11 | reverse primer used in cloning of wild type DNA polymerase II gene |
| 12 | molecular beacon template used in polymerase activity experiment |
| 13 | primer used in polymerase activity experiment |
| 14 | 5'-3' sequence used in exonuclease activity experiment |
| 15 | 3'-5'sequence used in exonuclease activity experiment |

The invention claimed is:

1. An isolated DNA polymerase derived 3'-5'exonuclease comprising an amino acid sequence which is at least 95% sequence identical over the entire length of the sequence with SEQ ID NO: 1, wherein the amino acid in position 442 is selected from the group consisting of Glu, Ala, Gly, Val, Leu, and Ile, the amino acid in position 445 is selected from the group consisting of Arg, Lys, and His, and/or the amino acid in position 568 is selected from the group consisting of Glu, Ala, Gly, Val, Leu, and Ile, wherein in the presence of dsDNA and dNTPs at 25° C., 5' overhangs are produced in 5 to 30 minutes.

2. The isolated DNA polymerase derived 3'-5'exonuclease according to claim 1, wherein said DNA polymerase derived 3'-5'exonuclease comprises an amino acid sequence selected from the group consisting of SEQ ID NOs: 3, 4, 5, 6, 7 and 8.

3. The isolated DNA polymerase derived 3'-5'exonuclease of claim 1, wherein the 5' overhang has a length of 10 to 40 nucleotides.

4. A composition comprising the isolated DNA polymerase derived 3'-5'exonuclease according to claim 1 and a buffer, a salt or a combination thereof.

5. A nucleic acid molecule encoding the isolated DNA polymerase derived 3'-5'exonuclease according to claim 1.

6. An expression vector comprising a nucleic acid molecule encoding an isolated DNA polymerase derived 3'-5'exonuclease according to claim 1 and regulatory sequences for the transcription and translation of the protein sequence encoded by said nucleic acid molecule.

7. A host cell comprising one or more expression vectors according to claim 6.

8. A method for preparation of a DNA polymerase derived 3'-5'exonuclease according to claim 1, comprising the steps of:

(a) culturing, in a culture medium, a host cell comprising a recombinant expression vector comprising a nucleic acid molecule encoding the DNA polymerase derived 3'-5'exonuclease according to claim 1 and regulatory sequences for the transcription of the nucleic acid molecule to form a transcript and translation of the transcript to provide the DNA polymerase derived 3'-5'exonuclease under conditions for the expression of the encoded DNA polymerase derived 3'-5' exonuclease; and (b) isolating or obtaining the DNA polymerase derived 3'-5' exonuclease from the host cell or from the culture medium or supernatant.

9. A method for removing contaminating polynucleotides from a sample, said method comprising contacting the sample with the DNA polymerase derived 3'-5'exonuclease according to claim 1.

10. A method for deleting a segment of one or more target double stranded nucleic acid molecules, the method comprising contacting one or more double stranded nucleic acid molecules and the DNA polymerase derived 3'-5'exonuclease according to claim 1, wherein said exonuclease cleaves nucleotides in a 3'-5' direction of the double stranded nucleic acid molecules to produce complementary single stranded 5' overhangs.

11. A method for assembly of two or more double stranded (ds) DNA molecules, said process comprising the steps of:

(a) providing two or more dsDNA molecules to be assembled, wherein the ends of the dsDNA molecules share a region of sequence identity;

(b) contacting the provided two or more DNA molecules with the DNA polymerase derived 3'-5' according to claim 1, whereby single stranded overhangs are generated in both ends of the provided dsDNA molecules, wherein gaps are formed during generation of the single-stranded overhangs;

(c) incubating the DNA molecules of (a) under conditions whereby said DNA molecules anneal through the overhang portions generated in step (b); and (d) optionally contacting the annealed molecules provided in step (c) with a DNA polymerase and allowing the DNA polymerase to fill in the gaps, wherein said DNA polymerase has reduced, impaired or inactivated strand displacement activity.

12. A process for inserting at least one target double stranded nucleic acid molecule into an acceptor nucleic acid molecule to provide a recombinant double stranded nucleic acid molecule, comprising:

(a) contacting the DNA polymerase derived 3'-5'exonuclease according to claim 1 and a blunt-ended target double stranded nucleic acid molecule, wherein said exonuclease cleaves nucleotides in 3'-5' direction of the blunt ends of the target stranded nucleic acid molecules to produce complementary single stranded 5' overhangs;

(b) contacting the DNA polymerase derived 3'-5'exonuclease according to claim 1 and a blunt-ended double stranded acceptor nucleic acid molecule, wherein said exonuclease cleaves nucleotides in 3'-5' direction of the blunt ends of said acceptor nucleic acid molecule to produce complementary single stranded 5' overhangs;

(c) providing a reaction mixture comprising the product of steps (a) and (b), a DNA polymerase, oligonucleotide primer(s) which is capable of annealing to a portion of the nucleic acid molecule of (a) and (b), and nucleotides; and (d) incubating said reaction mixture under conditions whereby the oligonucleotide primer(s) anneal to the nucleic acid molecules of step (a) and (b), and whereby the DNA polymerase extends said oligonucleotide primer(s) by polymerizing one or more nucleotides to produce a recombinant double stranded molecule.

\* \* \* \* \*

SEQUENCE LISTING

<160> NUMBER OF SEQ ID NOS: 15

<210> SEQ ID NO 1
<211> LENGTH: 810
<212> TYPE: PRT
<213> ORGANISM: Artificial Sequence

<220> FEATURE:
<223> OTHER INFORMATION: Moritella viscosa DNA polymerase derived 3'-5'
      exonuclease with variable amino acid positions
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (445)..(445)
<223> OTHER INFORMATION: Xaa can be any naturally occurring amino acid
<220> FEATURE:
<221> NAME/KEY: misc_feature
<222> LOCATION: (568)..(568)
<223> OTHER INFORMATION: Xaa can be any naturally occurring amino acid

<400> SEQUENCE: 1

Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
                20                  25                  30

Ala Val Lys Leu Ile Pro Ala Thr Gln Gln Leu Val Met Phe Ile Pro
            35                  40                  45

Gln Asp Gln Leu Thr Thr Ala Leu Ala Cys Leu Ser Glu Leu Asn Pro
        50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
            115                 120                 125

Phe Thr Gly Thr Pro Val Gln Arg Lys Gly Tyr Val Glu Phe Gln Gln
        130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
            180                 185                 190

Pro Phe Lys Arg Val Tyr Met Ile Gly Glu Gln Pro Glu Arg Asp Leu
        195                 200                 205

Ala Gln Thr Pro Glu Ser Glu Pro Leu Ile His Trp Val Ala Asp Glu
        210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
            260                 265                 270

Gly Gln Asn Leu His Trp Arg Asp Gly Arg Thr Pro Gln Gln Gln Gly
            275                 280                 285

Phe Leu Thr Leu His Gly Arg Val Val Val Asp Gly Ile Asp Ser Leu
        290                 295                 300

Lys Thr Ala Thr Tyr Ser Phe Pro Ser Phe Ser Leu Glu Asn Val Ala
305                 310                 315                 320

Gln Glu Ile Leu Gly Val Gly Lys Asp Thr Asp Asp Val Asp Asn Arg

-continued

```
            325                 330                 335

Met Glu Gln Ile Asn His Asp Phe His Phe Asn Lys Val Lys Leu Ala
            340                 345                 350

Lys Tyr Asn Leu Gln Asp Cys Val Leu Val Trp Asp Ile Phe Val Lys
            355                 360                 365

Thr Arg Leu Leu Asp Phe Leu Leu Leu Arg Ser Gln Leu Thr Gly Leu
    370                 375                 380

Glu Leu Asp Arg Asn Gly Gly Ser Val Leu Ala Phe Thr Asn Val Tyr
385                 390                 395                 400

Leu Pro Lys Leu His Arg Ala Gly Tyr Ile Ala Pro Asn Leu Arg Glu
                405                 410                 415

Ser Gly Val Met Ala Ser Pro Gly Gly Tyr Val Met Asp Ser Phe Pro
            420                 425                 430

Gly Leu Tyr Asp His Val Ile Val Leu Xaa Phe Lys Xaa Leu Tyr Pro
            435                 440                 445

Ser Ile Ile Arg Thr Phe Lys Ile Asp Pro Val Gly Leu Leu Glu Gly
    450                 455                 460

Val Gln Asn Pro Thr Glu Ala Ile Pro Gly Phe Arg Gly Gly Leu Phe
465                 470                 475                 480

Asp Arg Glu Lys His Tyr Leu Pro Asp Ile Ile Thr Glu Leu Trp Ser
                485                 490                 495

Gln Arg Asp Gln Ala Lys Leu Asp Lys Asp Ala Ala Arg Ser Gln Ala
            500                 505                 510

Ile Lys Ile Leu Met Asn Ser Phe Tyr Gly Val Leu Gly Ser Gly Gly
            515                 520                 525

Cys Arg Phe Tyr Asp Thr Arg Leu Ala Ser Ser Ile Thr Met Arg Gly
    530                 535                 540

Gln Glu Ile Met Gln Thr Thr Ala Lys Trp Ile Glu Glu Gln Gly Tyr
545                 550                 555                 560

Lys Val Ile Tyr Gly Asp Thr Xaa Ser Thr Phe Val Leu Leu Asp Ala
                565                 570                 575

Ala Lys Phe Thr Glu Gly Asp Arg Ser Glu Gln Ala Asp Arg Met Gly
            580                 585                 590

Lys Glu Leu Ser Glu Tyr Ile Asn Gln Gln Trp Gln Arg His Leu Arg
            595                 600                 605

Glu Asp Tyr Asp Ile Asp Cys Phe Leu Asp Ile Glu Tyr Glu Val His
    610                 615                 620

Tyr His Lys Phe Leu Met Pro Thr Ile Arg Gly Leu Asp Lys Gly Ser
625                 630                 635                 640

Lys Lys Arg Tyr Ala Gly Leu Val Asn Thr Lys Asp Gly Glu Lys Leu
                645                 650                 655

Ile Phe Lys Gly Leu Glu Thr Val Arg Thr Asp Trp Thr Asp Leu Ala
            660                 665                 670

Lys Met Phe Gln Met Glu Leu Tyr His Arg Val Phe His Gly Leu Ala
            675                 680                 685

Val Glu Asp Tyr Val Leu Glu Ile Val Glu Arg Thr Leu Ala Gly Glu
    690                 695                 700

Phe Asn Asp Lys Leu Val Tyr Arg Lys Arg Leu Arg Gln Glu Leu Ser
705                 710                 715                 720

Ala Tyr Val Lys Asn Val Pro Pro His Val Lys Ala Ala Arg Ala Ala
                725                 730                 735

Asp Glu Lys Asn Arg Gln Leu Gly Gln Pro Leu Arg Tyr Gln His Lys
            740                 745                 750
```

```
Ala Trp Ile Ser Tyr Val Leu Thr Leu Ser Gly Pro Glu Ala Val Glu
        755                 760                 765

His Gln His Ser Val Leu Asp Phe Glu His Tyr Ile Glu Lys Gln Ile
        770                 775                 780

Lys Pro Ile Ala Asp Gly Ile Leu Pro Phe Ile Gly Leu Ser Phe Asp
785                 790                 795                 800

Leu Ile Thr Asp Gln Gln Met Gly Leu Phe
                805                 810

<210> SEQ ID NO 2
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, wild type sequence

<400> SEQUENCE: 2

Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
            20                  25                  30

Ala Val Lys Leu Ile Pro Ala Thr Gln Gln Leu Val Met Phe Ile Pro
        35                  40                  45

Gln Asp Gln Leu Thr Thr Ala Leu Ala Cys Leu Ser Glu Leu Asn Pro
    50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
        115                 120                 125

Phe Thr Gly Thr Pro Val Gln Arg Lys Gly Tyr Val Glu Phe Gln Gln
    130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
            180                 185                 190

Pro Phe Lys Arg Val Tyr Met Ile Gly Glu Gln Pro Glu Arg Asp Leu
        195                 200                 205

Ala Gln Thr Pro Glu Ser Glu Pro Leu Ile His Trp Val Ala Asp Glu
    210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
            260                 265                 270

Gly Gln Asn Leu His Trp Arg Asp Gly Arg Thr Pro Gln Gln Gln Gly
        275                 280                 285

Phe Leu Thr Leu His Gly Arg Val Val Val Asp Gly Ile Asp Ser Leu
```

-continued

```
        290               295               300
Lys Thr Ala Thr Tyr Ser Phe Pro Ser Phe Ser Leu Glu Asn Val Ala
305               310               315               320

Gln Glu Ile Leu Gly Val Gly Lys Asp Thr Asp Asp Val Asp Asn Arg
              325               330               335

Met Glu Gln Ile Asn His Asp Phe His Phe Asn Lys Val Lys Leu Ala
              340               345               350

Lys Tyr Asn Leu Gln Asp Cys Val Leu Val Trp Asp Ile Phe Val Lys
              355               360               365

Thr Arg Leu Leu Asp Phe Leu Leu Leu Arg Ser Gln Leu Thr Gly Leu
              370               375               380

Glu Leu Asp Arg Asn Gly Gly Ser Val Leu Ala Phe Thr Asn Val Tyr
385               390               395               400

Leu Pro Lys Leu His Arg Ala Gly Tyr Ile Ala Pro Asn Leu Arg Glu
              405               410               415

Ser Gly Val Met Ala Ser Pro Gly Gly Tyr Val Met Asp Ser Phe Pro
              420               425               430

Gly Leu Tyr Asp His Val Ile Val Leu Asp Phe Lys Ser Leu Tyr Pro
              435               440               445

Ser Ile Ile Arg Thr Phe Lys Ile Asp Pro Val Gly Leu Leu Glu Gly
              450               455               460

Val Gln Asn Pro Thr Glu Ala Ile Pro Gly Phe Arg Gly Gly Leu Phe
465               470               475               480

Asp Arg Glu Lys His Tyr Leu Pro Asp Ile Ile Thr Glu Leu Trp Ser
              485               490               495

Gln Arg Asp Gln Ala Lys Leu Asp Lys Asp Ala Ala Arg Ser Gln Ala
              500               505               510

Ile Lys Ile Leu Met Asn Ser Phe Tyr Gly Val Leu Gly Ser Gly Gly
              515               520               525

Cys Arg Phe Tyr Asp Thr Arg Leu Ala Ser Ser Ile Thr Met Arg Gly
              530               535               540

Gln Glu Ile Met Gln Thr Thr Ala Lys Trp Ile Glu Glu Gln Gly Tyr
545               550               555               560

Lys Val Ile Tyr Gly Asp Thr Asp Ser Thr Phe Val Leu Leu Asp Ala
              565               570               575

Ala Lys Phe Thr Glu Gly Asp Arg Ser Glu Gln Ala Asp Arg Met Gly
              580               585               590

Lys Glu Leu Ser Glu Tyr Ile Asn Gln Gln Trp Gln Arg His Leu Arg
              595               600               605

Glu Asp Tyr Asp Ile Asp Cys Phe Leu Asp Ile Glu Tyr Glu Val His
              610               615               620

Tyr His Lys Phe Leu Met Pro Thr Ile Arg Gly Leu Asp Lys Gly Ser
625               630               635               640

Lys Lys Arg Tyr Ala Gly Leu Val Asn Thr Lys Asp Gly Glu Lys Leu
              645               650               655

Ile Phe Lys Gly Leu Glu Thr Val Arg Thr Asp Trp Thr Asp Leu Ala
              660               665               670

Lys Met Phe Gln Met Glu Leu Tyr His Arg Val Phe His Gly Leu Ala
              675               680               685

Val Glu Asp Tyr Val Leu Glu Ile Val Glu Arg Thr Leu Ala Gly Glu
              690               695               700

Phe Asn Asp Lys Leu Val Tyr Arg Lys Arg Leu Arg Gln Glu Leu Ser
705               710               715               720
```

-continued

```
Ala Tyr Val Lys Asn Val Pro Pro His Val Lys Ala Ala Arg Ala Ala
                725                 730                 735

Asp Glu Lys Asn Arg Gln Leu Gly Gln Pro Leu Arg Tyr Gln His Lys
                740                 745                 750

Ala Trp Ile Ser Tyr Val Leu Thr Leu Ser Gly Pro Glu Ala Val Glu
            755                 760                 765

His Gln His Ser Val Leu Asp Phe Glu His Tyr Ile Glu Lys Gln Ile
        770                 775                 780

Lys Pro Ile Ala Asp Gly Ile Leu Pro Phe Ile Gly Leu Ser Phe Asp
785                 790                 795                 800

Leu Ile Thr Asp Gln Gln Met Gly Leu Phe
                805                 810

<210> SEQ ID NO 3
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 3

Met Ser Ala Thr Tyr Leu Gly Phe Leu Leu Ser Arg His Ser Arg Asp
1                 5                  10                  15

Arg Asn Gly Asn Asn Glu Leu Ser Tyr Trp Leu Ala Ser Glu Met Gly
                20                  25                  30

Ala Val Lys Leu Ile Pro Ala Thr Gln Gln Leu Val Met Phe Ile Pro
            35                  40                  45

Gln Asp Gln Leu Thr Thr Ala Leu Ala Cys Leu Ser Glu Leu Asn Pro
        50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
        115                 120                 125

Phe Thr Gly Thr Pro Val Gln Arg Lys Gly Tyr Val Glu Phe Gln Gln
        130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
            180                 185                 190

Pro Phe Lys Arg Val Tyr Met Ile Gly Glu Gln Pro Glu Arg Asp Leu
        195                 200                 205

Ala Gln Thr Pro Glu Ser Glu Pro Leu Ile His Trp Val Ala Asp Glu
        210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
            245                 250                 255

Ala Gln Arg Ala Thr Phe His Asn Leu Lys Leu Ala Leu Gly Arg Gly
```

-continued

```
                260              265                270

Gly Gln Asn Leu His Trp Arg Asp Gly Arg Thr Pro Gln Gln Gln Gly
        275              280                285

Phe Leu Thr Leu His Gly Arg Val Val Val Asp Gly Ile Asp Ser Leu
    290              295              300

Lys Thr Ala Thr Tyr Ser Phe Pro Ser Phe Ser Leu Glu Asn Val Ala
305              310              315              320

Gln Glu Ile Leu Gly Val Gly Lys Asp Thr Asp Asp Val Asp Asn Arg
            325              330              335

Met Glu Gln Ile Asn His Asp Phe His Phe Asn Lys Val Lys Leu Ala
            340              345              350

Lys Tyr Asn Leu Gln Asp Cys Val Leu Val Trp Asp Ile Phe Val Lys
        355              360              365

Thr Arg Leu Leu Asp Phe Leu Leu Leu Arg Ser Gln Leu Thr Gly Leu
    370              375              380

Glu Leu Asp Arg Asn Gly Gly Ser Val Leu Ala Phe Thr Asn Val Tyr
385              390              395              400

Leu Pro Lys Leu His Arg Ala Gly Tyr Ile Ala Pro Asn Leu Arg Glu
            405              410              415

Ser Gly Val Met Ala Ser Pro Gly Gly Tyr Val Met Asp Ser Phe Pro
            420              425              430

Gly Leu Tyr Asp His Val Ile Val Leu Ala Phe Lys Ser Leu Tyr Pro
            435              440              445

Ser Ile Ile Arg Thr Phe Lys Ile Asp Pro Val Gly Leu Leu Glu Gly
        450              455              460

Val Gln Asn Pro Thr Glu Ala Ile Pro Gly Phe Arg Gly Gly Leu Phe
465              470              475              480

Asp Arg Glu Lys His Tyr Leu Pro Asp Ile Ile Thr Glu Leu Trp Ser
            485              490              495

Gln Arg Asp Gln Ala Lys Leu Asp Lys Asp Ala Ala Arg Ser Gln Ala
            500              505              510

Ile Lys Ile Leu Met Asn Ser Phe Tyr Gly Val Leu Gly Ser Gly Gly
        515              520              525

Cys Arg Phe Tyr Asp Thr Arg Leu Ala Ser Ser Ile Thr Met Arg Gly
        530              535              540

Gln Glu Ile Met Gln Thr Thr Ala Lys Trp Ile Glu Glu Gln Gly Tyr
545              550              555              560

Lys Val Ile Tyr Gly Asp Thr Asp Ser Thr Phe Val Leu Leu Asp Ala
            565              570              575

Ala Lys Phe Thr Glu Gly Asp Arg Ser Glu Gln Ala Asp Arg Met Gly
            580              585              590

Lys Glu Leu Ser Glu Tyr Ile Asn Gln Gln Trp Gln Arg His Leu Arg
            595              600              605

Glu Asp Tyr Asp Ile Asp Cys Phe Leu Asp Ile Glu Tyr Glu Val His
    610              615              620

Tyr His Lys Phe Leu Met Pro Thr Ile Arg Gly Leu Asp Lys Gly Ser
625              630              635              640

Lys Lys Arg Tyr Ala Gly Leu Val Asn Thr Lys Asp Gly Glu Lys Leu
            645              650              655

Ile Phe Lys Gly Leu Glu Thr Val Arg Thr Asp Trp Thr Asp Leu Ala
            660              665              670

Lys Met Phe Gln Met Glu Leu Tyr His Arg Val Phe His Gly Leu Ala
            675              680              685
```

-continued

```
Val Glu Asp Tyr Val Leu Glu Ile Val Glu Arg Thr Leu Ala Gly Glu
    690             695             700

Phe Asn Asp Lys Leu Val Tyr Arg Lys Arg Leu Arg Gln Glu Leu Ser
705             710             715             720

Ala Tyr Val Lys Asn Val Pro Pro His Val Lys Ala Ala Arg Ala Ala
            725             730             735

Asp Glu Lys Asn Arg Gln Leu Gly Gln Pro Leu Arg Tyr Gln His Lys
            740             745             750

Ala Trp Ile Ser Tyr Val Leu Thr Leu Ser Gly Pro Glu Ala Val Glu
            755             760             765

His Gln His Ser Val Leu Asp Phe Glu His Tyr Ile Glu Lys Gln Ile
    770             775             780

Lys Pro Ile Ala Asp Gly Ile Leu Pro Phe Ile Gly Leu Ser Phe Asp
785             790             795             800

Leu Ile Thr Asp Gln Gln Met Gly Leu Phe
                805             810

<210> SEQ ID NO 4
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 4

Met Ser Ala Thr Tyr Leu Gly Phe Leu Leu Ser Arg His Ser Arg Asp
1               5               10              15

Arg Asn Gly Asn Asn Glu Leu Ser Tyr Trp Leu Ala Ser Glu Met Gly
            20              25              30

Ala Val Lys Leu Ile Pro Ala Thr Gln Gln Leu Val Met Phe Ile Pro
            35              40              45

Gln Asp Gln Leu Thr Thr Ala Leu Ala Cys Leu Ser Glu Leu Asn Pro
    50              55              60

Arg Phe Thr Phe Lys Asp Leu Lys Met Arg Ser Phe Asp Leu Glu Leu
65              70              75              80

Met Ser Ala Phe Tyr Phe Arg Thr Ser His Asp Phe His Arg Ala Gln
            85              90              95

Glu Leu Leu Arg Arg Lys Leu Val Thr Val Leu Glu Ala Asp Ile Arg
            100             105             110

Pro Pro Glu Arg Tyr Leu Met Glu Arg Phe Ile Lys Gly Ala Val Glu
            115             120             125

Phe Thr Gly Thr Pro Val Gln Arg Lys Gly Tyr Val Glu Phe Gln Gln
    130             135             140

Ala Gln Leu Lys Pro Ala Glu Leu Pro Asp Asn Leu Val Asp Lys Ile
145             150             155             160

Lys Gln Ile Ser Leu Asp Ile Glu Cys Ser Glu His Gly Glu Leu Tyr
            165             170             175

Ser Ile Gly Leu Tyr Ser Leu Ser Pro Ala Tyr Cys Pro Asp Gly Gln
            180             185             190

Pro Phe Lys Arg Val Tyr Met Ile Gly Glu Gln Pro Glu Arg Asp Leu
            195             200             205

Ala Gln Thr Pro Glu Ser Glu Pro Leu Ile His Trp Val Ala Asp Glu
    210             215             220

Lys Ser Leu Leu Leu Ala Leu Gln Ala Phe Ala Ile Ser Tyr Asp Pro
```

-continued

```
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
                260                 265                 270

Gly Gln Asn Leu His Trp Arg Asp Gly Arg Thr Pro Gln Gln Gln Gly
                275                 280                 285

Phe Leu Thr Leu His Gly Arg Val Val Val Asp Gly Ile Asp Ser Leu
                290                 295                 300

Lys Thr Ala Thr Tyr Ser Phe Pro Ser Phe Ser Leu Glu Asn Val Ala
305                 310                 315                 320

Gln Glu Ile Leu Gly Val Gly Lys Asp Thr Asp Asp Val Asp Asn Arg
                325                 330                 335

Met Glu Gln Ile Asn His Asp Phe His Phe Asn Lys Val Lys Leu Ala
                340                 345                 350

Lys Tyr Asn Leu Gln Asp Cys Val Leu Val Trp Asp Ile Phe Val Lys
                355                 360                 365

Thr Arg Leu Leu Asp Phe Leu Leu Leu Arg Ser Gln Leu Thr Gly Leu
                370                 375                 380

Glu Leu Asp Arg Asn Gly Gly Ser Val Leu Ala Phe Thr Asn Val Tyr
385                 390                 395                 400

Leu Pro Lys Leu His Arg Ala Gly Tyr Ile Ala Pro Asn Leu Arg Glu
                405                 410                 415

Ser Gly Val Met Ala Ser Pro Gly Gly Tyr Val Met Asp Ser Phe Pro
                420                 425                 430

Gly Leu Tyr Asp His Val Ile Val Leu Asp Phe Lys Ser Leu Tyr Pro
                435                 440                 445

Ser Ile Ile Arg Thr Phe Lys Ile Asp Pro Val Gly Leu Leu Glu Gly
                450                 455                 460

Val Gln Asn Pro Thr Glu Ala Ile Pro Gly Phe Arg Gly Gly Leu Phe
465                 470                 475                 480

Asp Arg Glu Lys His Tyr Leu Pro Asp Ile Ile Thr Glu Leu Trp Ser
                485                 490                 495

Gln Arg Asp Gln Ala Lys Leu Asp Lys Asp Ala Ala Arg Ser Gln Ala
                500                 505                 510

Ile Lys Ile Leu Met Asn Ser Phe Tyr Gly Val Leu Gly Ser Gly Gly
                515                 520                 525

Cys Arg Phe Tyr Asp Thr Arg Leu Ala Ser Ser Ile Thr Met Arg Gly
                530                 535                 540

Gln Glu Ile Met Gln Thr Thr Ala Lys Trp Ile Glu Glu Gln Gly Tyr
545                 550                 555                 560

Lys Val Ile Tyr Gly Asp Thr Ala Ser Thr Phe Val Leu Leu Asp Ala
                565                 570                 575

Ala Lys Phe Thr Glu Gly Asp Arg Ser Glu Gln Ala Asp Arg Met Gly
                580                 585                 590

Lys Glu Leu Ser Glu Tyr Ile Asn Gln Gln Trp Gln Arg His Leu Arg
                595                 600                 605

Glu Asp Tyr Asp Ile Asp Cys Phe Leu Asp Ile Glu Tyr Glu Val His
                610                 615                 620

Tyr His Lys Phe Leu Met Pro Thr Ile Arg Gly Leu Asp Lys Gly Ser
625                 630                 635                 640

Lys Lys Arg Tyr Ala Gly Leu Val Asn Thr Lys Asp Gly Glu Lys Leu
                645                 650                 655
```

-continued

```
Ile Phe Lys Gly Leu Glu Thr Val Arg Thr Asp Trp Thr Asp Leu Ala
            660                 665                 670

Lys Met Phe Gln Met Glu Leu Tyr His Arg Val Phe His Gly Leu Ala
            675                 680                 685

Val Glu Asp Tyr Val Leu Glu Ile Val Glu Arg Thr Leu Ala Gly Glu
            690                 695                 700

Phe Asn Asp Lys Leu Val Tyr Arg Lys Arg Leu Arg Gln Glu Leu Ser
705                 710                 715                 720

Ala Tyr Val Lys Asn Val Pro Pro His Val Lys Ala Ala Arg Ala Ala
            725                 730                 735

Asp Glu Lys Asn Arg Gln Leu Gly Gln Pro Leu Arg Tyr Gln His Lys
            740                 745                 750

Ala Trp Ile Ser Tyr Val Leu Thr Leu Ser Gly Pro Glu Ala Val Glu
            755                 760                 765

His Gln His Ser Val Leu Asp Phe Glu His Tyr Ile Glu Lys Gln Ile
            770                 775                 780

Lys Pro Ile Ala Asp Gly Ile Leu Pro Phe Ile Gly Leu Ser Phe Asp
785                 790                 795                 800

Leu Ile Thr Asp Gln Gln Met Gly Leu Phe
            805                 810
```

```
<210> SEQ ID NO 5
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 5
```

```
Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
            20                  25                  30

Ala Val Lys Leu Ile Pro Ala Thr Gln Gln Leu Val Met Phe Ile Pro
            35                  40                  45

Gln Asp Gln Leu Thr Thr Ala Leu Ala Cys Leu Ser Glu Leu Asn Pro
            50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
            85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
            115                 120                 125

Phe Thr Gly Thr Pro Val Gln Arg Lys Gly Tyr Val Glu Phe Gln Gln
            130                 135                 140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
            165                 170                 175

Ser Ile Gly Leu Tyr Ser Leu Ser Pro Ala Tyr Cys Pro Asp Gly Gln
            180                 185                 190

Pro Phe Lys Arg Val Tyr Met Ile Gly Glu Gln Pro Glu Arg Asp Leu
```

-continued

```
                195                 200                 205

Ala Gln Thr Pro Glu Ser Glu Pro Leu Ile His Trp Val Ala Asp Glu
    210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
                260                 265                 270

Gly Gln Asn Leu His Trp Arg Asp Gly Arg Thr Pro Gln Gln Gln Gly
                275                 280                 285

Phe Leu Thr Leu His Gly Arg Val Val Val Asp Gly Ile Asp Ser Leu
    290                 295                 300

Lys Thr Ala Thr Tyr Ser Phe Pro Ser Phe Ser Leu Glu Asn Val Ala
305                 310                 315                 320

Gln Glu Ile Leu Gly Val Gly Lys Asp Thr Asp Asp Val Asp Asn Arg
                325                 330                 335

Met Glu Gln Ile Asn His Asp Phe His Phe Asn Lys Val Lys Leu Ala
                340                 345                 350

Lys Tyr Asn Leu Gln Asp Cys Val Leu Val Trp Asp Ile Phe Val Lys
                355                 360                 365

Thr Arg Leu Leu Asp Phe Leu Leu Leu Arg Ser Gln Leu Thr Gly Leu
    370                 375                 380

Glu Leu Asp Arg Asn Gly Gly Ser Val Leu Ala Phe Thr Asn Val Tyr
385                 390                 395                 400

Leu Pro Lys Leu His Arg Ala Gly Tyr Ile Ala Pro Asn Leu Arg Glu
                405                 410                 415

Ser Gly Val Met Ala Ser Pro Gly Gly Tyr Val Met Asp Ser Phe Pro
                420                 425                 430

Gly Leu Tyr Asp His Val Ile Val Leu Glu Phe Lys Ser Leu Tyr Pro
                435                 440                 445

Ser Ile Ile Arg Thr Phe Lys Ile Asp Pro Val Gly Leu Leu Glu Gly
    450                 455                 460

Val Gln Asn Pro Thr Glu Ala Ile Pro Gly Phe Arg Gly Gly Leu Phe
465                 470                 475                 480

Asp Arg Glu Lys His Tyr Leu Pro Asp Ile Ile Thr Glu Leu Trp Ser
                485                 490                 495

Gln Arg Asp Gln Ala Lys Leu Asp Lys Asp Ala Ala Arg Ser Gln Ala
                500                 505                 510

Ile Lys Ile Leu Met Asn Ser Phe Tyr Gly Val Leu Gly Ser Gly Gly
                515                 520                 525

Cys Arg Phe Tyr Asp Thr Arg Leu Ala Ser Ser Ile Thr Met Arg Gly
    530                 535                 540

Gln Glu Ile Met Gln Thr Thr Ala Lys Trp Ile Glu Glu Gln Gly Tyr
545                 550                 555                 560

Lys Val Ile Tyr Gly Asp Thr Asp Ser Thr Phe Val Leu Leu Asp Ala
                565                 570                 575

Ala Lys Phe Thr Glu Gly Asp Arg Ser Glu Gln Ala Asp Arg Met Gly
                580                 585                 590

Lys Glu Leu Ser Glu Tyr Ile Asn Gln Gln Trp Gln Arg His Leu Arg
                595                 600                 605

Glu Asp Tyr Asp Ile Asp Cys Phe Leu Asp Ile Glu Tyr Glu Val His
    610                 615                 620
```

```
Tyr His Lys Phe Leu Met Pro Thr Ile Arg Gly Leu Asp Lys Gly Ser
625             630         635             640

Lys Lys Arg Tyr Ala Gly Leu Val Asn Thr Lys Asp Gly Glu Lys Leu
                645             650             655

Ile Phe Lys Gly Leu Glu Thr Val Arg Thr Asp Trp Thr Asp Leu Ala
            660             665             670

Lys Met Phe Gln Met Glu Leu Tyr His Arg Val Phe His Gly Leu Ala
        675             680             685

Val Glu Asp Tyr Val Leu Glu Ile Val Glu Arg Thr Leu Ala Gly Glu
        690             695             700

Phe Asn Asp Lys Leu Val Tyr Arg Lys Arg Leu Arg Gln Glu Leu Ser
705             710             715             720

Ala Tyr Val Lys Asn Val Pro Pro His Val Lys Ala Ala Arg Ala Ala
            725             730             735

Asp Glu Lys Asn Arg Gln Leu Gly Gln Pro Leu Arg Tyr Gln His Lys
            740             745             750

Ala Trp Ile Ser Tyr Val Leu Thr Leu Ser Gly Pro Glu Ala Val Glu
            755             760             765

His Gln His Ser Val Leu Asp Phe Glu His Tyr Ile Glu Lys Gln Ile
    770             775             780

Lys Pro Ile Ala Asp Gly Ile Leu Pro Phe Ile Gly Leu Ser Phe Asp
785             790             795             800

Leu Ile Thr Asp Gln Gln Met Gly Leu Phe
            805             810
```

<210> SEQ ID NO 6
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 6

```
Met Ser Ala Thr Tyr Leu Gly Phe Leu Leu Ser Arg His Ser Arg Asp
1               5               10              15

Arg Asn Gly Asn Asn Glu Leu Ser Tyr Trp Leu Ala Ser Glu Met Gly
            20              25              30

Ala Val Lys Leu Ile Pro Ala Thr Gln Gln Leu Val Met Phe Ile Pro
        35              40              45

Gln Asp Gln Leu Thr Thr Ala Leu Ala Cys Leu Ser Glu Leu Asn Pro
    50              55              60

Arg Phe Thr Phe Lys Asp Leu Lys Met Arg Ser Phe Asp Leu Glu Leu
65              70              75              80

Met Ser Ala Phe Tyr Phe Arg Thr Ser His Asp Phe His Arg Ala Gln
            85              90              95

Glu Leu Leu Arg Arg Lys Leu Val Thr Val Leu Glu Ala Asp Ile Arg
            100             105             110

Pro Pro Glu Arg Tyr Leu Met Glu Arg Phe Ile Lys Gly Ala Val Glu
        115             120             125

Phe Thr Gly Thr Pro Val Gln Arg Lys Gly Tyr Val Glu Phe Gln Gln
        130             135             140

Ala Gln Leu Lys Pro Ala Glu Leu Pro Asp Asn Leu Val Asp Lys Ile
145             150             155             160

Lys Gln Ile Ser Leu Asp Ile Glu Cys Ser Glu His Gly Glu Leu Tyr
```

-continued

```
                165             170             175

Ser Ile Gly Leu Tyr Ser Leu Ser Pro Ala Tyr Cys Pro Asp Gly Gln
            180             185             190

Pro Phe Lys Arg Val Tyr Met Ile Gly Glu Gln Pro Glu Arg Asp Leu
            195             200             205

Ala Gln Thr Pro Glu Ser Glu Pro Leu Ile His Trp Val Ala Asp Glu
            210             215             220

Lys Ser Leu Leu Leu Ala Leu Gln Ala Phe Ala Ile Ser Tyr Asp Pro
225             230             235             240

Asp Ile Phe Ile Gly Trp Asn Val Ile Asn Phe Asp Phe Arg Leu Leu
            245             250             255

Ala Gln Arg Ala Thr Phe His Asn Leu Lys Leu Ala Leu Gly Arg Gly
            260             265             270

Gly Gln Asn Leu His Trp Arg Asp Gly Arg Thr Pro Gln Gln Gln Gly
            275             280             285

Phe Leu Thr Leu His Gly Arg Val Val Val Asp Gly Ile Asp Ser Leu
            290             295             300

Lys Thr Ala Thr Tyr Ser Phe Pro Ser Phe Ser Leu Glu Asn Val Ala
305             310             315             320

Gln Glu Ile Leu Gly Val Gly Lys Asp Thr Asp Asp Val Asp Asn Arg
            325             330             335

Met Glu Gln Ile Asn His Asp Phe His Phe Asn Lys Val Lys Leu Ala
            340             345             350

Lys Tyr Asn Leu Gln Asp Cys Val Leu Val Trp Asp Ile Phe Val Lys
            355             360             365

Thr Arg Leu Leu Asp Phe Leu Leu Leu Arg Ser Gln Leu Thr Gly Leu
            370             375             380

Glu Leu Asp Arg Asn Gly Gly Ser Val Leu Ala Phe Thr Asn Val Tyr
385             390             395             400

Leu Pro Lys Leu His Arg Ala Gly Tyr Ile Ala Pro Asn Leu Arg Glu
            405             410             415

Ser Gly Val Met Ala Ser Pro Gly Gly Tyr Val Met Asp Ser Phe Pro
            420             425             430

Gly Leu Tyr Asp His Val Ile Val Leu Asp Phe Lys Ser Leu Tyr Pro
            435             440             445

Ser Ile Ile Arg Thr Phe Lys Ile Asp Pro Val Gly Leu Leu Glu Gly
            450             455             460

Val Gln Asn Pro Thr Glu Ala Ile Pro Gly Phe Arg Gly Gly Leu Phe
465             470             475             480

Asp Arg Glu Lys His Tyr Leu Pro Asp Ile Ile Thr Glu Leu Trp Ser
            485             490             495

Gln Arg Asp Gln Ala Lys Leu Asp Lys Asp Ala Ala Arg Ser Gln Ala
            500             505             510

Ile Lys Ile Leu Met Asn Ser Phe Tyr Gly Val Leu Gly Ser Gly Gly
            515             520             525

Cys Arg Phe Tyr Asp Thr Arg Leu Ala Ser Ser Ile Thr Met Arg Gly
            530             535             540

Gln Glu Ile Met Gln Thr Thr Ala Lys Trp Ile Glu Glu Gln Gly Tyr
545             550             555             560

Lys Val Ile Tyr Gly Asp Thr Glu Ser Thr Phe Val Leu Leu Asp Ala
            565             570             575

Ala Lys Phe Thr Glu Gly Asp Arg Ser Glu Gln Ala Asp Arg Met Gly
            580             585             590
```

-continued

```
Lys Glu Leu Ser Glu Tyr Ile Asn Gln Gln Trp Gln Arg His Leu Arg
        595                 600             605

Glu Asp Tyr Asp Ile Asp Cys Phe Leu Asp Ile Glu Tyr Glu Val His
    610                 615             620

Tyr His Lys Phe Leu Met Pro Thr Ile Arg Gly Leu Asp Lys Gly Ser
625                 630             635                 640

Lys Lys Arg Tyr Ala Gly Leu Val Asn Thr Lys Asp Gly Glu Lys Leu
                645             650             655

Ile Phe Lys Gly Leu Glu Thr Val Arg Thr Asp Trp Thr Asp Leu Ala
            660             665             670

Lys Met Phe Gln Met Glu Leu Tyr His Arg Val Phe His Gly Leu Ala
        675             680             685

Val Glu Asp Tyr Val Leu Glu Ile Val Glu Arg Thr Leu Ala Gly Glu
    690             695             700

Phe Asn Asp Lys Leu Val Tyr Arg Lys Arg Leu Arg Gln Glu Leu Ser
705             710             715                 720

Ala Tyr Val Lys Asn Val Pro Pro His Val Lys Ala Ala Arg Ala Ala
            725             730             735

Asp Glu Lys Asn Arg Gln Leu Gly Gln Pro Leu Arg Tyr Gln His Lys
            740             745             750

Ala Trp Ile Ser Tyr Val Leu Thr Leu Ser Gly Pro Glu Ala Val Glu
        755             760             765

His Gln His Ser Val Leu Asp Phe Glu His Tyr Ile Glu Lys Gln Ile
    770             775             780

Lys Pro Ile Ala Asp Gly Ile Leu Pro Phe Ile Gly Leu Ser Phe Asp
785             790             795                 800

Leu Ile Thr Asp Gln Gln Met Gly Leu Phe
                805             810

<210> SEQ ID NO 7
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 7

Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
            20                  25                  30

Ala Val Lys Leu Ile Pro Ala Thr Gln Gln Leu Val Met Phe Ile Pro
        35                  40                  45

Gln Asp Gln Leu Thr Thr Ala Leu Ala Cys Leu Ser Glu Leu Asn Pro
    50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
                85                  90                  95

Glu Leu Leu Arg Arg Lys Leu Val Thr Val Leu Glu Ala Asp Ile Arg
            100                 105                 110

Pro Pro Glu Arg Tyr Leu Met Glu Arg Phe Ile Lys Gly Ala Val Glu
        115                 120                 125

Phe Thr Gly Thr Pro Val Gln Arg Lys Gly Tyr Val Glu Phe Gln Gln
```

-continued

```
        130                    135                    140

Ala Gln Leu Lys Pro Ala Glu Leu Pro Asp Asn Leu Val Asp Lys Ile
145                 150                 155                 160

Lys Gln Ile Ser Leu Asp Ile Glu Cys Ser Glu His Gly Glu Leu Tyr
                165                 170                 175

Ser Ile Gly Leu Tyr Ser Leu Ser Pro Ala Tyr Cys Pro Asp Gly Gln
                180                 185                 190

Pro Phe Lys Arg Val Tyr Met Ile Gly Glu Gln Pro Glu Arg Asp Leu
                195                 200                 205

Ala Gln Thr Pro Glu Ser Glu Pro Leu Ile His Trp Val Ala Asp Glu
        210                 215                 220

Lys Ser Leu Leu Leu Ala Leu Gln Ala Phe Ala Ile Ser Tyr Asp Pro
225                 230                 235                 240

Asp Ile Phe Ile Gly Trp Asn Val Ile Asn Phe Asp Phe Arg Leu Leu
                245                 250                 255

Ala Gln Arg Ala Thr Phe His Asn Leu Lys Leu Ala Leu Gly Arg Gly
                260                 265                 270

Gly Gln Asn Leu His Trp Arg Asp Gly Arg Thr Pro Gln Gln Gln Gly
                275                 280                 285

Phe Leu Thr Leu His Gly Arg Val Val Val Asp Gly Ile Asp Ser Leu
        290                 295                 300

Lys Thr Ala Thr Tyr Ser Phe Pro Ser Phe Ser Leu Glu Asn Val Ala
305                 310                 315                 320

Gln Glu Ile Leu Gly Val Gly Lys Asp Thr Asp Asp Val Asp Asn Arg
                325                 330                 335

Met Glu Gln Ile Asn His Asp Phe His Phe Asn Lys Val Lys Leu Ala
                340                 345                 350

Lys Tyr Asn Leu Gln Asp Cys Val Leu Val Trp Asp Ile Phe Val Lys
                355                 360                 365

Thr Arg Leu Leu Asp Phe Leu Leu Leu Arg Ser Gln Leu Thr Gly Leu
        370                 375                 380

Glu Leu Asp Arg Asn Gly Gly Ser Val Leu Ala Phe Thr Asn Val Tyr
385                 390                 395                 400

Leu Pro Lys Leu His Arg Ala Gly Tyr Ile Ala Pro Asn Leu Arg Glu
                405                 410                 415

Ser Gly Val Met Ala Ser Pro Gly Gly Tyr Val Met Asp Ser Phe Pro
                420                 425                 430

Gly Leu Tyr Asp His Val Ile Val Leu Ala Phe Lys Ser Leu Tyr Pro
                435                 440                 445

Ser Ile Ile Arg Thr Phe Lys Ile Asp Pro Val Gly Leu Leu Glu Gly
        450                 455                 460

Val Gln Asn Pro Thr Glu Ala Ile Pro Gly Phe Arg Gly Gly Leu Phe
465                 470                 475                 480

Asp Arg Glu Lys His Tyr Leu Pro Asp Ile Ile Thr Glu Leu Trp Ser
                485                 490                 495

Gln Arg Asp Gln Ala Lys Leu Asp Lys Asp Ala Ala Arg Ser Gln Ala
                500                 505                 510

Ile Lys Ile Leu Met Asn Ser Phe Tyr Gly Val Leu Gly Ser Gly Gly
                515                 520                 525

Cys Arg Phe Tyr Asp Thr Arg Leu Ala Ser Ser Ile Thr Met Arg Gly
        530                 535                 540

Gln Glu Ile Met Gln Thr Thr Ala Lys Trp Ile Glu Glu Gln Gly Tyr
545                 550                 555                 560
```

-continued

```
Lys Val Ile Tyr Gly Asp Thr Ala Ser Thr Phe Val Leu Leu Asp Ala
            565                 570                 575

Ala Lys Phe Thr Glu Gly Asp Arg Ser Glu Gln Ala Asp Arg Met Gly
            580                 585                 590

Lys Glu Leu Ser Glu Tyr Ile Asn Gln Gln Trp Gln Arg His Leu Arg
            595                 600                 605

Glu Asp Tyr Asp Ile Asp Cys Phe Leu Asp Ile Glu Tyr Glu Val His
            610                 615                 620

Tyr His Lys Phe Leu Met Pro Thr Ile Arg Gly Leu Asp Lys Gly Ser
625                 630                 635                 640

Lys Lys Arg Tyr Ala Gly Leu Val Asn Thr Lys Asp Gly Glu Lys Leu
            645                 650                 655

Ile Phe Lys Gly Leu Glu Thr Val Arg Thr Asp Trp Thr Asp Leu Ala
            660                 665                 670

Lys Met Phe Gln Met Glu Leu Tyr His Arg Val Phe His Gly Leu Ala
            675                 680                 685

Val Glu Asp Tyr Val Leu Glu Ile Val Glu Arg Thr Leu Ala Gly Glu
            690                 695                 700

Phe Asn Asp Lys Leu Val Tyr Arg Lys Arg Leu Arg Gln Glu Leu Ser
705                 710                 715                 720

Ala Tyr Val Lys Asn Val Pro Pro His Val Lys Ala Ala Arg Ala Ala
            725                 730                 735

Asp Glu Lys Asn Arg Gln Leu Gly Gln Pro Leu Arg Tyr Gln His Lys
            740                 745                 750

Ala Trp Ile Ser Tyr Val Leu Thr Leu Ser Gly Pro Glu Ala Val Glu
            755                 760                 765

His Gln His Ser Val Leu Asp Phe Glu His Tyr Ile Glu Lys Gln Ile
            770                 775                 780

Lys Pro Ile Ala Asp Gly Ile Leu Pro Phe Ile Gly Leu Ser Phe Asp
785                 790                 795                 800

Leu Ile Thr Asp Gln Gln Met Gly Leu Phe
            805                 810

<210> SEQ ID NO 8
<211> LENGTH: 810
<212> TYPE: PRT
<213> ORGANISM: Artificial Sequence
<220> FEATURE:
<223> OTHER INFORMATION: Moritella viscosa DNA polymerase derived 3'-5'
      exonuclease, modified by mutagenesis

<400> SEQUENCE: 8

Met Ser Ala Thr Tyr Leu Gly Phe Leu Leu Ser Arg His Ser Arg Asp
1               5                   10                  15

Arg Asn Gly Asn Asn Glu Leu Ser Tyr Trp Leu Ala Ser Glu Met Gly
            20                  25                  30

Ala Val Lys Leu Ile Pro Ala Thr Gln Gln Leu Val Met Phe Ile Pro
            35                  40                  45

Gln Asp Gln Leu Thr Thr Ala Leu Ala Cys Leu Ser Glu Leu Asn Pro
            50                  55                  60

Arg Phe Thr Phe Lys Asp Leu Lys Met Arg Ser Phe Asp Leu Glu Leu
65                  70                  75                  80

Met Ser Ala Phe Tyr Phe Arg Thr Ser His Asp Phe His Arg Ala Gln
            85                  90                  95

Glu Leu Leu Arg Arg Lys Leu Val Thr Val Leu Glu Ala Asp Ile Arg
```

-continued

```
                100              105              110

Pro Pro Glu Arg Tyr Leu Met Glu Arg Phe Ile Lys Gly Ala Val Glu
            115              120              125

Phe Thr Gly Thr Pro Val Gln Arg Lys Gly Tyr Val Glu Phe Gln Gln
    130              135              140

Ala Gln Leu Lys Pro Ala Glu Leu Pro Asp Asn Leu Val Asp Lys Ile
145              150              155              160

Lys Gln Ile Ser Leu Asp Ile Glu Cys Ser Glu His Gly Glu Leu Tyr
                165              170              175

Ser Ile Gly Leu Tyr Ser Leu Ser Pro Ala Tyr Cys Pro Asp Gly Gln
                180              185              190

Pro Phe Lys Arg Val Tyr Met Ile Gly Glu Gln Pro Glu Arg Asp Leu
            195              200              205

Ala Gln Thr Pro Glu Ser Glu Pro Leu Ile His Trp Val Ala Asp Glu
    210              215              220

Lys Ser Leu Leu Leu Ala Leu Gln Ala Phe Ala Ile Ser Tyr Asp Pro
225              230              235              240

Asp Ile Phe Ile Gly Trp Asn Val Ile Asn Phe Asp Phe Arg Leu Leu
            245              250              255

Ala Gln Arg Ala Thr Phe His Asn Leu Lys Leu Ala Leu Gly Arg Gly
            260              265              270

Gly Gln Asn Leu His Trp Arg Asp Gly Arg Thr Pro Gln Gln Gln Gly
            275              280              285

Phe Leu Thr Leu His Gly Arg Val Val Val Asp Gly Ile Asp Ser Leu
    290              295              300

Lys Thr Ala Thr Tyr Ser Phe Pro Ser Phe Ser Leu Glu Asn Val Ala
305              310              315              320

Gln Glu Ile Leu Gly Val Gly Lys Asp Thr Asp Val Asp Asn Arg
            325              330              335

Met Glu Gln Ile Asn His Asp Phe His Phe Asn Lys Val Lys Leu Ala
            340              345              350

Lys Tyr Asn Leu Gln Asp Cys Val Leu Val Trp Asp Ile Phe Val Lys
            355              360              365

Thr Arg Leu Leu Asp Phe Leu Leu Leu Arg Ser Gln Leu Thr Gly Leu
    370              375              380

Glu Leu Asp Arg Asn Gly Gly Ser Val Leu Ala Phe Thr Asn Val Tyr
385              390              395              400

Leu Pro Lys Leu His Arg Ala Gly Tyr Ile Ala Pro Asn Leu Arg Glu
            405              410              415

Ser Gly Val Met Ala Ser Pro Gly Gly Tyr Val Met Asp Ser Phe Pro
            420              425              430

Gly Leu Tyr Asp His Val Ile Val Leu Asp Phe Lys Arg Leu Tyr Pro
            435              440              445

Ser Ile Ile Arg Thr Phe Lys Ile Asp Pro Val Gly Leu Leu Glu Gly
    450              455              460

Val Gln Asn Pro Thr Glu Ala Ile Pro Gly Phe Arg Gly Gly Leu Phe
465              470              475              480

Asp Arg Glu Lys His Tyr Leu Pro Asp Ile Ile Thr Glu Leu Trp Ser
            485              490              495

Gln Arg Asp Gln Ala Lys Leu Asp Lys Asp Ala Ala Arg Ser Gln Ala
            500              505              510

Ile Lys Ile Leu Met Asn Ser Phe Tyr Gly Val Leu Gly Ser Gly Gly
            515              520              525
```

-continued

```
Cys Arg Phe Tyr Asp Thr Arg Leu Ala Ser Ser Ile Thr Met Arg Gly
    530                 535                 540

Gln Glu Ile Met Gln Thr Thr Ala Lys Trp Ile Glu Glu Gln Gly Tyr
545                 550                 555                 560

Lys Val Ile Tyr Gly Asp Thr Asp Ser Thr Phe Val Leu Leu Asp Ala
                565                 570                 575

Ala Lys Phe Thr Glu Gly Asp Arg Ser Glu Gln Ala Asp Arg Met Gly
                580                 585                 590

Lys Glu Leu Ser Glu Tyr Ile Asn Gln Gln Trp Gln Arg His Leu Arg
            595                 600                 605

Glu Asp Tyr Asp Ile Asp Cys Phe Leu Asp Ile Glu Tyr Glu Val His
    610                 615                 620

Tyr His Lys Phe Leu Met Pro Thr Ile Arg Gly Leu Asp Lys Gly Ser
625                 630                 635                 640

Lys Lys Arg Tyr Ala Gly Leu Val Asn Thr Lys Asp Gly Glu Lys Leu
                645                 650                 655

Ile Phe Lys Gly Leu Glu Thr Val Arg Thr Asp Trp Thr Asp Leu Ala
                660                 665                 670

Lys Met Phe Gln Met Glu Leu Tyr His Arg Val Phe His Gly Leu Ala
                675                 680                 685

Val Glu Asp Tyr Val Leu Glu Ile Val Glu Arg Thr Leu Ala Gly Glu
    690                 695                 700

Phe Asn Asp Lys Leu Val Tyr Arg Lys Arg Leu Arg Gln Glu Leu Ser
705                 710                 715                 720

Ala Tyr Val Lys Asn Val Pro Pro His Val Lys Ala Ala Arg Ala Ala
                725                 730                 735

Asp Glu Lys Asn Arg Gln Leu Gly Gln Pro Leu Arg Tyr Gln His Lys
                740                 745                 750

Ala Trp Ile Ser Tyr Val Leu Thr Leu Ser Gly Pro Glu Ala Val Glu
            755                 760                 765

His Gln His Ser Val Leu Asp Phe Glu His Tyr Ile Glu Lys Gln Ile
    770                 775                 780

Lys Pro Ile Ala Asp Gly Ile Leu Pro Phe Ile Gly Leu Ser Phe Asp
785                 790                 795                 800

Leu Ile Thr Asp Gln Gln Met Gly Leu Phe
                805                 810
```

```
<210> SEQ ID NO 9
<211> LENGTH: 2433
<212> TYPE: DNA
<213> ORGANISM: Artificial Sequence
<220> FEATURE:
<223> OTHER INFORMATION: Moritella viscosa DNA polymerase derived 3'-5'
      exonuclease, encoding wild type sequence

<400> SEQUENCE: 9
atgtctgcta catatctggg tttttttatta tcgcgccata gccgtgatcg taatggtaac        60
aatgaattaa gctactggtt agcatctgaa atgggtgcgg ttaaactgat cccggcaacc       120
cagcagctgg tgatgttcat tcctcaagat caacttacca ctgcattagc ttgtttaagt       180
gagttgaatc cgcgctttac ctttaaagac ttgaaaatgc gtagctttga tttagaactt       240
atgagcgcct tttatttccg tacttcccat gattttcacc gcgcacaaga gttattaaga       300
cgtaagctgg ttacggtatt agaagccgat attcgcccac ctgagcgtta cttaatggag       360
cgttttatca aaggcgcagt cgagttcact ggtacgcctg tacaacgtaa aggctatgtt       420
```

-continued

```
gaatttcaac aagcacagct taaaccagct gaactgccag ataacttagt cgataaaata    480
aaacagatct cactggatat cgaatgttca gaacacggag agctttactc tattggtttg    540
tattccctaa gccctgctta ttgcccagat ggtcagccct ttaaacgggt atacatgata    600
ggtgagcagc ctgagcgcga tttagcacaa actcctgaaa gcgagccgtt aatccattgg    660
gttgccgacg agaaaagttt attactggcg ctgcaagcat tcgcgatcag ttacgatccc    720
gacattttta ttggttggaa tgtaattaac tttgatttcc gtttattagc ccaacgtgcc    780
acattccata atcttaaatt agcattgggt cgaggtgggc aaaacctgca ttggcgagat    840
ggccgtaccc cacagcaaca aggctttctg actttacacg gtcgggtggt cgttgatggt    900
attgatagtt taaaaacggc aacttatagc ttcccaagtt ttagtttaga aaacgtggca    960
caagagattc tcggtgttgg taaagatact gatgatgtcg ataatcgcat ggaacagatt   1020
aaccacgact ttcattttaa caaggtaaaa ctggcgaaat acaacctgca agattgcgtc   1080
ttagtgtggg atatttttgt taaaacccgt ttgttagatt ttttattact acgctcgcag   1140
ttaaccggtt tagaactaga tcgtaacggt ggatcggtat tggcgtttac caatgtgtat   1200
cttcctaagt tacatcgcgc gggttatatc gcgccaaatc tgcgtgagag tggggtaatg   1260
gcaagtcctg gcggttatgt gatggattca tttcctggct tgtatgatca tgtcatcgta   1320
ctggatttta aaagtctgta tccgtcaatt attcgcacct ttaaaattga tccggtaggg   1380
ttgctagaag gggttcaaaa cccgactgag gcgattccgg gtttccgtgg tggtttgttt   1440
gatcgtgaaa agcattacct tcccgatatt attaccgaac tgtggtcgca gcgcgatcaa   1500
gccaaactcg ataaagatgc tgcccgttca caggccatta aaatcttaat gaattcgttt   1560
tatggtgtgt tagggtcggg cggttgtcgt ttttatgata ctcgtttagc ctcgtcgatc   1620
accatgcgtg ggcaagaaat catgcagact accgcaaaat ggatcgaaga gcagggatat   1680
aaggtgattt atggcgatac cgattccacc tttgtattac tcgatgccgc caagtttacc   1740
gagggtgatc gtagcgaaca agccgatcgc atgggcaaag agctgtcaga atatattaac   1800
cagcagtggc aacgacacct acgtgaagat tacgatatcg actgtttctt agatattgaa   1860
tacgaagtgc attatcacaa gttttttaatg ccgactatcc gtggcttgga taaaggcagt   1920
aaaaagcgct atgccggatt agtgaatacc aaagatggtg aaaaacttat tttttaaaggg   1980 ctggaaaccg tacgtaccga ttggactgac ttagccaaga tgttccaaat ggagttatac   2040
catcgggtat ttcatggctt agcagtcgaa gattatgtac tggaaattgt agaaaggacc   2100
ttagcgggtg agtttaacga taagttagtt tatcgtaagc gtttacgcca agaattgtct   2160
gcttatgtga agaacgtgcc gccacatgta aaagcggcgc gtgctgctga tgagaagaat   2220
cgccaattag ggcaaccgtt acgttatcag cataaagcgt ggatcagtta tgtgttaacc   2280
ctaagtggcc ctgaagctgt cgagcatcaa cattcggtac tcgattttga gcattacatt   2340
gaaaaacaaa ttaaacccat tgctgatggt atcttgcctt ttattggctt gagttttgat   2400
ttgataaccg atcaacaaat gggattattt taa                                2433
```

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10

-continued

```
caccttgtct gctacatatc tgggt                                              25

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
ttaaaataat cccatttgtt gatcggttat ca                                     32

<210> SEQ ID NO 12
<211> LENGTH: 82
<212> TYPE: DNA
<213> ORGANISM: Artificial Sequence
<220> FEATURE:
<223> OTHER INFORMATION: molecular beacon template

<400> SEQUENCE: 12
ggcccgtagg aggaaaggac atcttctagc atacgggccg tcaagttcat ggccagtcaa       60
gtcgtcagaa atttcgcacc ac                                                82

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
gtggtgcgaa atttctgac                                                    19

<210> SEQ ID NO 14
<211> LENGTH: 40
<212> TYPE: DNA
<213> ORGANISM: Artificial Sequence
<220> FEATURE:
<223> OTHER INFORMATION: primer

<400> SEQUENCE: 14
tatccaccaa tactaccccta cgatactttg tccactcaat                             40

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
ataggtggtt atgatgggat gctatgaaac aggtgagtta                              40
```